US011717511B2

(12) United States Patent
Kweon et al.

(10) Patent No.: US 11,717,511 B2
(45) Date of Patent: Aug. 8, 2023

(54) PHARMACEUTICAL COMPOSITION COMPRISING DERIVATIVE COMPOUND OF 1,2-NAPHTHOQUINONE FOR PREVENTING OR TREATING SOLID CANCER OR BLOOD CANCER

(71) Applicant: HUEN Co., Ltd., Cheonan-si (KR)

(72) Inventors: Ki Ryang Kweon, Daejeon (KR); Jun Young Heo, Jeonju-si (KR); Min Ho Shong, Daejeon (KR); Jeong Su Han, Daejeon (KR); Min Jeong Ryu, Daejeon (KR)

(73) Assignee: HUEN CO., LTD., Cheonan-si (KR)

( * ) Notice: Subject to any disclaimer, the term of this patent is extended or adjusted under 35 U.S.C. 154(b) by 232 days.

(21) Appl. No.: 16/618,289

(22) PCT Filed: Apr. 4, 2019

(86) PCT No.: PCT/KR2019/004001
§ 371 (c)(1),
(2) Date: Nov. 29, 2019

(87) PCT Pub. No.: WO2019/198976
PCT Pub. Date: Oct. 17, 2019

(65) Prior Publication Data
US 2021/0155596 A1 May 27, 2021

(30) Foreign Application Priority Data

Apr. 9, 2018 (KR) ........................ 10-2018-0040884
Apr. 9, 2018 (KR) ........................ 10-2018-0040895
Apr. 9, 2018 (KR) ........................ 10-2018-0040913

(51) Int. Cl.
*C07D 263/60* (2006.01)
*C07D 413/04* (2006.01)
*C07D 417/04* (2006.01)
*C07D 401/04* (2006.01)
*C07D 405/04* (2006.01)
*A61P 35/00* (2006.01)
*A61P 35/02* (2006.01)
*A61K 31/4184* (2006.01)
*A61K 31/4192* (2006.01)
*A61K 31/423* (2006.01)
*A61K 31/428* (2006.01)
*A61K 31/4745* (2006.01)

(52) U.S. Cl.
CPC ...... *A61K 31/4184* (2013.01); *A61K 31/4192* (2013.01); *A61K 31/423* (2013.01); *A61K 31/428* (2013.01); *A61K 31/4745* (2013.01); *A61P 35/00* (2018.01); *A61P 35/02* (2018.01); *C07D 263/60* (2013.01); *C07D 401/04* (2013.01); *C07D 405/04* (2013.01); *C07D 413/04* (2013.01); *C07D 417/04* (2013.01)

(58) Field of Classification Search
CPC .. C07D 263/60; C07D 413/04; C07D 417/04; C07D 401/04; C07D 405/04; A61P 35/00; A61P 35/02
See application file for complete search history.

(56) References Cited

U.S. PATENT DOCUMENTS

2016/0376243 A1 12/2016 Lee et al.
2016/0376258 A1 12/2016 Lee et al.

FOREIGN PATENT DOCUMENTS

| CN | 109481438 A | * | 3/2019 |
|----|----|----|----|
| JP | 2010-525053 A | | 7/2010 |
| JP | 2017-501204 A | | 1/2017 |
| JP | 2017-502976 A | | 1/2017 |
| KR | 10-2008-0096419 A | | 10/2008 |
| KR | 101501612 B1 | | 3/2015 |
| KR | 10-2015-0080423 A | | 7/2015 |
| KR | 10-2015-0080425 A | | 7/2015 |
| KR | 10-2015-0080426 A | | 7/2015 |
| KR | 10-2016-0116211 A | | 10/2016 |
| KR | 10-2016-0116296 A | | 10/2016 |
| WO | 2008-066294 A1 | | 6/2008 |
| WO | 2015-102370 A1 | | 7/2015 |
| WO | 2017-035982 A1 | | 3/2017 |
| WO | 2018-005279 A1 | | 1/2018 |

OTHER PUBLICATIONS

Machine translation of CN 109481438-A, 2022.*
International Search Report issued for International Application No. PCT/KR2019/004001 dated Jul. 16, 2019, 3 pages.
Li et al., "Novel naphtho[2,1-d]oxazole-4,5-diones as NQO1 substrates with improved aqueous solubility: Design, synthesis, and in vivo antitumor evaluation", Bioorganic & Medicinal Chemistry, 2016, vol. 24, No. 5, pp. 1006-1013.
Huang, et al., "Identification of ortho-naphthoquinones as anti-AML agents by highly efficient oxidation of phenols", Bioorganic Chemistry 86 (2019) 97-102.
Carroll et al., "Synthesis of 2-Alkylnaphth{2,1-d}oxazole-4,5-diones", Chemical communications, 1969, pp. 923-924.

(Continued)

*Primary Examiner* — Sun Jae Yoo
(74) *Attorney, Agent, or Firm* — Rothwell, Figg, Ernst & Manbeck, P.C.

(57) ABSTRACT

The present invention relates to a pharmaceutical composition for preventing or treating solid cancer and blood cancers such as acute leukemia and chronic leukemia, comprising a derivative compound of 1,2-naphthoquinone or a pharmaceutically acceptable salt thereof as an effective component. The derivative compound of 1,2-naphthoquinone is highly effective in killing cancer cells of various solid cancers, acute leukemia, and chronic leukemia, and thus can be beneficially used as a pharmaceutical composition for preventing or treating cancers, especially solid cancers, acute leukemia, and chronic leukemia.

11 Claims, 9 Drawing Sheets

(56) References Cited

OTHER PUBLICATIONS

Chauhan and McKinnon, "Some reactions of ethyl azidoformate with quinones", Canadian Journal of Chemistry, 1977, vol. 55, pp. 2363-2372.
Bova, et al., "The oxidative mechanism of action of ortho-quinone inhibitors of protein-tyrosine phosphatase α is mediated by hydrogen peroxide", Biochemistry and Biophysics, vol. 429, No. 1, Sep. 1, 2004, pp. 30-41.
European Search Report issued for European Patent Application No. 14877254.4 dated Apr. 19, 2017, 8 pages.
Extended European Search Report issued in European Patent Application No. 19 784 600.9 dated Nov. 9, 2021, 12 pages.

* cited by examiner

PHARMACEUTICAL COMPOSITION COMPRISING DERIVATIVE COMPOUND OF 1,2-NAPHTHOQUINONE FOR PREVENTING OR TREATING SOLID CANCER OR BLOOD CANCER

CROSS-REFERENCE TO RELATED APPLICATIONS

This application is a 35 U.S.C. 371 National Phase Entry Application from PCT/KR2019/004001, filed on Apr. 4, 2019, which claims priorities to and the benefits of Korean Patent Application Nos. 10-2018-0040913, 10-2018-0040884, and 10-2018-0040895 filed on 9 Apr. 2018, the entire contents of which are incorporated herein by reference in their entirety.

TECHNICAL FIELD

The present disclosure relates to a pharmaceutical composition containing a 1,2-naphthoquinone derivative compound for preventing or treating cancer, for example, solid cancer, and blood cancer, such as acute leukemia and chronic leukemia.

BACKGROUND ART

Cells are the smallest constituent unit of the body, and divide and grow by regulatory functions thereof under normal conditions. When the lifespan of cells end or cells are damaged, the cells themselves die and thus maintain the balance of overall cell number. However, if there are problems with the regulatory functions of cells themselves due to various causes, abnormal cells, which would die normally, proliferate excessively, and in some cases, infiltrate into surrounding tissues and organs to thereby form masses and destroy or deform existing structures. Such a condition may be defined as cancer.

Cancer is one of the incurable diseases that humanity should solve, and huge capital is being invested in the development for curing cancer worldwide, and medical technology is also being developed, nevertheless cancer death continues to increase. According to the Statistics Korea, about 220,000 new cancer patients were reported in Korea as of 2012, and such a figure is about twice the number of new cancer patients in 2002, and the number of cancer patients is increasing rapidly every year. About 70,000 out of 220,000 cancer patients died of cancer, and therefore, the development of therapeutics for cancer treatment is urgent.

Currently, the treatments of cancer patients depend on surgical procedures, radiotherapy, and chemotherapy (administering about 40 drugs showing strong cytotoxicity), but most of these treatments are limited to early cancer patients or particular cancer, and thus cancer deaths are still on the rise.

Meanwhile, leukemia is divided into acute and chronic leukemia depending on the degree of cell differentiation, i.e., the rate of aggravation, and divided into myeloid and lymphoid leukemia according to the origin of cells. Therefore, leukemia is classified into acute myeloid leukemia, acute lymphoblastic leukemia, chronic myeloid leukemia, and chronic lymphocytic leukemia.

Acute leukemia is a disease that excessively produces abnormal leukocyte progenitor cells or platelet progenitor cells, wherein the proliferation of myeloid cells is called acute myeloid leukemia (AML) and the proliferation of lymphoid cells is called acute lymphoblastic leukemia (ALL). Since abnormal leukocytes increase to occupy blood-making locations, normal leukocytes, erythrocytes, platelets, and the like are not formed, and thus infections or bleeding occur easily, and untreated infections or bleeding results in a death within several months. The recent development of chemotherapy significantly improved the survival rate in infants with acute leukemia, but the survival rate is still low in adults.

Acute myeloid leukemia is a malignant tumor that occurs in stem cells of non-lymphocytic leukocytes or myeloid leukocytes produced from the bone marrow, and a hematopoietic tumor in which a genetic mutation occurring in hematopoietic stem cells stops the differentiation of myeloid progenitor cells at several stages, causing immature myoblasts to proliferate into monoclonal cells. Acute myeloid leukemia manifests bone marrow dysfunction, such as anemia, fever, an increased susceptibility to infections, and bleeding tendency, and in some cases, shows organ infiltration of tumor cells, such as enlarged spleen and lymph node swelling.

Acute lymphoid leukemia is a blood cancer that occurs in lymphocyte lineage cells in blood and bone marrow, and is known to be caused by mutations of several genes involved in proliferation, differentiation, maturation, and disruption of the lymphocyte lineage cells. The causes of genetic mutations in acute lymphoid leukemia are currently not clearly revealed, but genetic predispositions, viruses, multiple carcinogens, ionizing radiation, and the like are assumed to be involved in acute lymphoid leukemia, like in other cancers. Similar to other leukemia symptoms, the symptoms observed in acute lymphoblastic leukemia occur when the formation of normal blood cells is disturbed by abnormal leukemia cells or abnormal leukemia cells infiltrate into organs, such as lymph nodes, the spleen, the liver, the brain, and the spinal cord. Chronic myeloid leukemia is caused by a Philadelphia chromosome produced by a transition, which is a translocation of two pieces obtained by truncating predetermined portions from human chromosomes 9 and 22. Chronic myeloid leukemia is a disease that occurs due to excessive proliferation of abnormal cells in the bone marrow caused by abnormal enlargement of hematopoietic stem cell clones having the Philadelphia chromosome. Chronic myeloid leukemia accounts for about 25% of all adult leukemia. Chronic myeloid leukemia is also called adult leukemia since the disease frequently occurs in people aged 30-50 years and the older people, but chronic myeloid leukemia may occur in all ages and also occur in children and adolescents.

A Philadelphia chromosome produces BCR-ABL fusion protein having activity of abnormal tyrosine kinase due to the BCR-ABL fusion gene obtained by the fusion of ABL gene on chromosome 9 and BCR gene on chromosome 22 through chromosomal translocation. The activation of abnormal tyrosine kinase brings about abnormal amplification of malignant cells, thereby causing blood cancer.

Gleevec® (imatinib) is a medicine, which competitively binds to the adenosine triphosphate (ATP)-binding site of the BCR-ABL fusion protein to thereby inhibit enzymatic activity of the protein. However, some patients become resistant to Gleevec® due to the BCR-ABL gene mutation, resulting in disease aggravation. The occurrence of patient groups with Gleevec® limits and resistance has led to the development of second-generation (nilotinib) and third-generation (dasatinib) tyrosine kinase inhibitors, but these drugs also have disadvantages that these drugs fail to achieve complete treatment and the success rate of treatment in acute patients is increased by only 30%. Therefore, studies for the treatment of chronic myeloid leukemia are continuously needed.

Chronic lymphocytic leukemia is a disease in which lymphocytes as a kind of leukocytes grow into tumors and thus excessively proliferate in the bone marrow, thereby disturbing the production of normal blood cells. The reduction of normal leukocytes increases the risk of infection, reduces erythrocytes to cause anemia, and reduces platelets having a hemostatic action to cause an increased hemostasis time. Chronic lymphocytic leukemia is very rare in Korea but frequently occurs in USA. In most cases, chronic lymphocytic leukemia occurs in men after 50 years of age. The cause of chronic lymphocytic leukemia has not yet been identified, and is not associated with environments, occupations, viruses, and irradiation. However, immediate family members with chronic lymphocytic leukemia are more than three times more likely to develop chronic lymphocytic leukemia or other lymphoproliferative diseases than the general population, and chronic lymphocytic leukemia occurs about 10 years faster when there is a family history than when there is no family history.

Standard methods for treating leukemia include chemotherapy, hematopoietic stem cell transplantation, radiotherapy, and the like, and in a case of chemotherapy, a combination of two or more anticancer drugs is usually included. Ideal chemotherapy is that anti-leukemic agents do not inhibit normal hemostasis, cause no other harmful side effects, and show a selective effect for only leukemic cells. However, most of anti-leukemic agents can kill leukemia cells somewhat close to the ideal state, but also inhibit normal hemostasis and cause other harmful side effects, and thus are limited to the treatment of leukemia. Furthermore, the anti-leukemic agents have a weak antitumor effect and may cause side effects, and thus cannot implement sufficient chemotherapy, in drug-resistant leukemia cells.

Hematopoietic stem cell transplantation (HSCT) refers to, currently, the transplantation, as a transplantation source, every type of hematopoietic stem cells existing in peripheral blood (PB) and cord blood (CB), beyond the area of bone marrow transplantation (BMT) using bone marrow in the past. Hematopoietic stem cell transplantation is a treatment in which new hematopoietic stem cells are transplanted into hematological tumor patients after removal of cancer cells and the patient's own hematopoietic stem cells using chemotherapy and radiotherapy. Hematopoietic stem cell transplantation has become an effective and promising treatment in various areas, such as not only leukemia, aplastic anemia, and malignant lymphoma, which are represented by leukemia, but also refractory autoimmune diseases and solid cancer, beyond the limited concept of early bone marrow transplantation. However, the hematopoietic stem cell transplantation so far is a treatment with a high risk of complications due to high-dose chemotherapy and graft-versus-host disease after allograft.

Therefore, for effective cancer treatment, it is important to establish and apply a treatment schedule suitable for each cancer patient by using various methods, such as radiotherapy, surgery therapy, and chemotherapy. In addition, the development of novel therapy drugs for treating various types of cancer, for example, solid cancer and blood cancer, is an important task given to the art.

Meanwhile, Korean Patent Publication Nos. 10-2015-0080423, 10-2015-0080425, and 10-2015-0080426, which are prior art documents associated with 1,2-naphthoquinone derivative compounds, disclose 1,2-naphthoquinone derivatives and manufacturing methods therefor, but do not disclose that 1,2-naphthoquinone derivative compounds having the structure of the present disclosure, with respect to a composition for treatment of a metabolic disease, have a treatment effect on solid cancer, and blood cancer, such as acute leukemia and chronic leukemia.

PRIOR ART DOCUMENTS

Patent Documents (Patent Document 1) Korean Patent Publication No. 10-2015-0080423 (1,2-naphthoquinone derivative and preparation method therefor, 9 Jul. 2015)

(Patent Document 2) Korean Patent Publication No. 10-2015-0080425 (1,2-naphthoquinone derivative and preparation method therefor, 9 Jul. 2015)

(Patent Document 3) Korean Patent Publication No. 10-2015-0080426 (1,2-naphthoquinone derivative and preparation method therefor, 9 Jul. 2015)

DETAILED DESCRIPTION OF THE INVENTION

Technical Problem

An aspect of the present disclosure is to provide a pharmaceutical composition containing a 1,2-naphthoquinone derivative compound for preventing or treating solid cancer or blood cancer.

Technical Solution

In accordance with an aspect of the present disclosure, there is provided a pharmaceutical composition for preventing or treating solid cancer or blood cancer, the composition containing a 1,2-naphthoquinone derivative compound represented by Formula 1 below or a pharmaceutically acceptable salt thereof as an active ingredient. In a preferable aspect, the blood cancer is acute leukemia, chronic leukemia, drug-resistant chronic leukemia, or refractory acute leukemia.

[Formula 1]

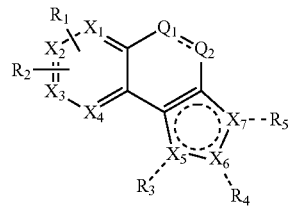

In Formula 1, $R_1$ and $R_2$ are each independently hydrogen, halogen, hydroxy, $C_1$-$C_6$ alkoxy, $C_1$-$C_6$ alkyl, $C_4$-$C_{10}$ aryl, $C_4$-$C_{10}$ aryloxy, $C_2$-$C_{10}$ heteroaryl, —$NO_2$, —$NR'_1R'_2$, —$NR'_1(CO(O)R'_2)$, —$NR'_1(C(O)NR'_1R'_2)$, —$CO(O)R'_1$, —$C(O)NR'_1R'_2$, —$CN$, —$SO(O)R'_1$, —$SO(O)NR'_1R'_2$, $NR'_1(SO(O)R'_2)$, or —$CSNR'_1R'_2$, or $R_4$ and $R_2$ may form a cyclic structure of $C_4$-$C_{10}$ aryl or a cyclic structure of $C_2$-$C_{10}$ heteroaryl by mutual coupling, wherein $R'_1$ and $R'_2$ are each independently hydrogen, $C_1$-$C_6$ alkyl, $C_3$-$C_8$ cycloalkyl, $C_4$-$C_{10}$ aryl, $C_4$-$C_{10}$ aryloxy, $C_1$-$C_8$ heteroaryl, —$(CR''_1R''_2)_m$—$C_4$-$C_{10}$ aryl, —$(CR''_1R''_2)_m$—$C_4$-$C_{10}$ heteroaryl, or $NR''_1R''_2$, wherein $R''_1$ and $R''_2$ each are independently hydrogen or $C_1$-$C_3$ alkyl, or $R''_1$ and $R''_2$ may form a cyclic structure of $C_4$-$C_{10}$ aryl by mutual coupling;

$R_3$, $R_4$, and $R_5$ are each independently hydrogen, halogen, hydroxy, $C_1$-$C_6$ alkyl, $C_2$-$C_{10}$ alkene, $C_1$-$C_6$ alkoxy, $C_3$-$C_8$ cycloalkyl, $C_2$-$C_8$ heterocycloalkyl, $C_4$-$C_{10}$ aryl, $C_4$-$C_{10}$ aryloxy, $C_4$-$C_8$ heteroaryl, —(CR'$_5$R'$_6$)$_m$—C$_4$-C$_{10}$ aryl, —(CR'$_5$R'$_6$)$_m$—C$_4$-C$_{10}$ aryloxy, —(CR'$_5$R'$_6$)$_m$—C$_1$-C$_8$ heteroaryl, —(CR'$_5$R'$_6$)$_m$—NR'$_3$R'$_4$, —(CR'$_5$R'$_6$)$_m$—C$_3$-C$_8$ heterocycloalkyl, —(CR'$_5$R'$_6$)$_m$—OR'$_3$, —(CR'$_5$R'$_6$)$_m$(O)COR'$_3$, —CO(O)R'$_3$, —CONR'$_3$R'$_4$, —NR'$_3$R'$_4$, —NR'$_3$(C(O)R'$_4$), —SO(O)R'$_3$, —SO(O)NR'$_3$R'$_4$, NR'$_3$(SO(O)R'$_4$), —CSNR'$_3$R'$_4$, —CH$_2$A when a compound of formula (1) is "A", or -A when a compound of formula (1) is "A", wherein R'$_3$ and R'$_4$ are each independently hydrogen, $C_1$-$C_6$ alkyl, $C_3$-$C_8$ cycloalkyl, $C_4$-$C_{10}$ aryl, —(CR'$_5$R'$_6$)$_m$—C$_4$-C$_{10}$ aryl, —(CR'$_5$R'$_6$)$_m$—C$_4$-C$_{10}$ aryloxy, (CR'$_5$R'$_6$)$_m$—C$_1$-C$_{10}$ heteroaryl, or —CO(O)R''$_3$, or R'$_3$ and R'$_4$ may form a cyclic structure of $C_2$-$C_{10}$ heterocycloalkyl or a cyclic structure of $C_4$-$C_{10}$ heteroaryl by mutual coupling, and R'$_5$ and R'$_6$ are each independently hydrogen or $C_1$-$C_3$ alkyl, wherein R''$_3$ is $C_1$-$C_6$ alkyl;

$Q_1$ and $Q_2$ are each independently CO, COR$_6$, or COR$_7$, $Q_1$ and $Q_2$ form a single bond when $Q_4$ is CO and $Q_2$ is CO, $Q_1$ and $Q_2$ form a double bond when $Q_4$ is COR$_6$ and $Q_2$ is COR$_7$, $R_6$ and $R_7$ are each independently hydrogen, $C_4$-$C_{10}$ alkoxy, $C_1$-$C_6$ alkyl, $C_4$-$C_{10}$ aryl, $C_4$-$C_{10}$ aryloxy, $C_2$-$C_{10}$ heteroaryl, —CO(O)R'$_7$, —C(O) NR'$_7$R'$_8$, —SO(O)R'$_7$, SO(O)NR'$_7$R'$_8$, —SO$_3$R'$_7$, —PO$_3$R'$_7$, or —CSNR'$_7$R'$_8$, or R$_6$ and R$_7$ may form a cyclic structure of $C_3$-$C_{10}$ heterocycloalkyl or a cyclic structure of $C_3$-$C_{10}$ heteroaryl by mutual coupling, wherein R'$_7$ and R'$_8$ are each independently hydrogen, $C_1$-$C_6$ alkyl, $C_3$-$C_8$ cycloalkyl, $C_4$-$C_{10}$ aryl, $C_4$-$C_{10}$ aryloxy, $C_4$-$C_8$ heteroaryl, or —(CR''$_1$R''$_5$)m'—C$_4$-C$_{10}$ aryl, wherein R''$_4$ and R'' are each independently hydrogen or $C_4$-$C_3$ alkyl;

when $Q_1$ is a cyclic structure of substituted or unsubstituted $C_3$-$C_5$ heterocycloalkyl and $Q_2$ is CO, or $Q_4$ is CO and $Q_2$ is a cyclic structure of substituted or unsubstituted $C_3$-$C_5$ heterocycloalkyl, $Q_4$ and $Q_2$ form a single bond, m and m' are each independently an integer of 1 to 4;

a heteroatom is at least one selected from N, O, and S;

$X_1$ to $X_4$ are each independently CH or N(R''$_6$), wherein R''$_6$ is hydrogen or $C_1$-$C_3$ alkyl;

$X_5$, $X_6$, and $X_7$ are each independently N, O, or S, with the proviso except that both $X_5$ and $X_6$ are N, both $X_6$ and $X_7$ are N, or both $X_5$ and $X_7$ are N; and the sign ≈≈≈≈ represents a single bond or a double bond, the sign ---- represents a single bond or represents that a bond may not be formed, and the sign

represents that a cyclic structure containing the sign may be or may not be an aromatic.

The term "alkyl" refers to a single-bonded, straight- or branched-chain hydrocarbon group, and examples thereof may include $C_{1-10}$ alkyl, specifically, $C_{1-6}$ alkyl, and more specifically methyl, ethyl, propyl, n-butyl, isobutyl, tert-butyl, and 1-methylpropyl.

The term "alkoxy" refers to an oxygen group to which a single-bonded, straight- or branched-chain saturated hydrocarbon group is attached, and examples thereof may include $C_{1-10}$ alkoxy, specifically, $C_{1-6}$ alkoxy, and more specifically methoxy, ethoxy, propoxy, n-butoxy, tert-butoxy, and 1-methylpropoxy.

The term "cycloalkyl" refers to a ring-shaped, single-bonded, saturated hydrocarbon group, and examples thereof may include $C_{3-10}$ cycloalkyl, specifically, $C_3$-$C_8$ cycloalkyl, and more specifically, cyclopropyl, cyclobutyl, cyclopentyl, and cyclohexyl, according to the number of carbon atoms.

The term "heterocycloalkyl" refers to a ring-shaped, single-bonded saturated hydrocarbon group containing, as a ring-constituting atom, at least one heteroatom, such as N, O, or S, in addition to a carbon atom, and examples thereof may include $C_2$-$C_3$ heterocycloalkyl, $C_2$-$C_{10}$ heterocycloalkyl, or $C_2$-$C_5$ heterocycloalkyl containing at least one, specifically, one to three heteroatoms selected from the group consisting of N, O, and S according to the number and kind of heteroatoms and the number of carbon atoms contained in the ring, and more specifically, aziridine, pyrrolidine, pyrrolidinyl, piperidinyl, piperazinyl, morpholinyl, tetrahydrofuranyl, or tetrahydropyranyl.

The term "aryl" refers to an aromatic substituent having at least one ring having a covalent pi electron system, and includes monocyclic or fused ring polycyclic (that is, rings sharing adjacent pairs of carbon atoms) groups. Examples of the aryl include $C_4$-$C_{10}$ aryl, more specifically, $C_6$-$C_{10}$, and still more specifically, phenyl and naphthyl, according to the number of carbon atoms contained in the ring.

The term "heteroaryl" refers to an aromatic ring compound containing, as a ring-constituting atom, at least one heteroatom, such as N, O, or S, in addition to a carbon atom, and examples thereof may include $C_1$-$C_{10}$ heteroaryl, more specifically, $C_1$-$C_8$ heteroaryl, $C_2$-$C_{10}$ heteroaryl, or $C_2$-$C_5$ heteroaryl, containing at least one, specifically one to three heteroatoms selected from the group consisting of N, O, and S according to the number and kind of heteroatoms and the number of carbon atoms contained in the ring.

Examples of the aryl or heteroaryl may include phenyl, naphthyl, furanyl, pyranyl, oxazolyl, isoxazolyl, pyridyl, pyrazinyl, pyrimidyl, pyridazinyl, oxadiazolyl, thiadiazolyl, tetrazolyl, triazinyl, and triazyl, but are not limited thereto.

The term "aryloxy" refers to a group in which an oxygen atom is attached to any one of the carbon atoms constituting an aromatic substituent, and for example, —O—C$_6$H$_5$ or —C$_6$H$_4$—O— may be expressed when oxygen is attached to a phenyl group.

Herein, the "substituent" may be at least one, preferably one to three, selected from the group consisting of halo, hydroxy, cyano, nitro, unsubstituted or substituted alkyl, unsubstituted or substituted alkenyl, unsubstituted or substituted alkynyl, unsubstituted or substituted alkoxy, unsubstituted or substituted alkoxycarbonyl, unsubstituted or substituted cycloalkyl, unsubstituted or substituted heterocycloalkyl, unsubstituted or substituted aryl, unsubstituted and substituted heteroaryl. Specifically, the substituent may be at least one selected from the group consisting of hydroxy, halo, $C_1$-$C_{10}$ alkyl, $C_2$-$C_{10}$ alkenyl, $C_2$-$C_{10}$ alkynyl, $C_1$-$C_{10}$ alkoxy, $C_1$-$C_{10}$ alkoxycarbonyl, $C_3$-$C_8$ cycloalkyl, $C_2$-$C_8$ heterocycloalkyl, $C_4$-$C_{10}$ aryl, and $C_2$-$C_{10}$ heteroaryl.

In addition, a prodrug containing the 1,2-naphthoquinone derivative compound of the present disclosure is regarded as one kind of the compound of Formula 1 except that $Q_1$ is CO and $Q_2$ is CO.

Preferably, in Formula 1, $R_3$ is hydrogen, halogen, hydroxy, $C_1$-$C_6$ alkyl, $C_1$-$C_6$ alkoxy, $C_3$-$C_8$ cycloalkyl, (CR'$_5$R'$_6$)$_m$—C$_4$-C$_{10}$ aryl, —(CR'$_5$R'$_6$)$_m$—OR'$_3$, —CO(O)R'$_3$, —CH$_2$A when a compound of formula (1) is "A", or -A when a compound of formula (1) is "A", wherein R'₃ is hydrogen, $C_1$-$C_6$ alkyl, $C_3$-$C_8$ cycloalkyl, $C_4$-$C_{10}$ aryl, —(CR'₅R'₆)ₘ—$C_4$-$C_{10}$ aryl, —(CR'₅R'₅)ₘ—$C_4$-$C_{10}$ aryloxy, —(CR'₅R'₆)ₘ—$C_1$-$C_{10}$ heteroaryl, or —CO(O)R"₃, wherein R'₅ and R'₆ are each independently hydrogen or $C_1$-$C_3$ alkyl, and R"₃ is $C_1$-$C_6$ alkyl;

R₄ is hydrogen, halogen, hydroxy, $C_1$-$C_6$ alkyl, $C_2$-$C_{10}$ alkene, $C_1$-$C_6$ alkoxy, $C_3$-$C_8$ cycloalkyl, $C_2$-$C_8$ heterocycloalkyl, $C_4$-$C_{10}$ aryl, $C_4$-$C_{10}$ aryloxy, $C_1$-$C_8$ heteroaryl, —(CR'₅R'₆)ₘ—$C_4$-$C_{10}$ aryl, —(CR'₅R'₆)ₘ—$C_4$-$C_{10}$ aryloxy, —(CR'₅R'₆)ₘ—$C_1$-$C_8$ heteroaryl, —(CR'₅R'₆)ₘ—NR'₃R'₄, —(CR'₅R'₆)ₘ—$C_3$-$C_8$ heterocycloalkyl, —(CR'₅R'₆)ₘ—OR'₃, (CR'₅R'₆)ₘ(O)COR'₃, —CO(O)R'₃, —CONR'₃R'₄, —NR'₃R'₄, NR'₃(C(O)R'₄), or -A when a compound of formula (1) is "A", wherein R'₃ and R'₄ are each independently hydrogen, $C_3$-$C_6$ alkyl, $C_3$-$C_8$ cycloalkyl, $C_4$-$C_{10}$ aryl, —(CR'₅R'₆)ₘ—$C_4$-$C_{10}$ aryl, —(CR'₅R'₆)ₘ—$C_4$-$C_{10}$ aryloxy, —(CR'₅R'₆)ₘ—$C_1$-$C_{10}$ heteroaryl, or —CO(O)R"₃, or R'₃ and R'₄ may form a cyclic structure of $C_2$-$C_{10}$ heterocycloalkyl or a cyclic structure of $C_1$-$C_{10}$ heteroaryl by mutual coupling, and R'₅ and R'₆ are each independently hydrogen or $C_1$-$C_3$ alkyl, wherein R"₃ is $C_1$-$C_6$ alkyl;

R₅ is hydrogen, halogen, hydroxy, $C_1$-$C_6$ alkyl, $C_2$-$C_{10}$ alkene, $C_1$-$C_6$ alkoxy, $C_3$-$C_8$ cycloalkyl, $C_2$-$C_8$ heterocycloalkyl, $C_4$-$C_{10}$ aryl, $C_4$-$C_{10}$ aryloxy, $C_4$-$C_8$ heteroaryl, —(CR'₅R'₆)ₘ—$C_4$-$C_{10}$ aryl, —(CR'₅R'₆)ₘ—$C_4$-$C_{10}$ aryloxy, —(CR'₅R'₆)ₘ—$C_1$-$C_8$ heteroaryl, —(CR'₅R'₆)ₙ—NR'₃R'₄, —(CR'₅R'₆)ₘ—$C_3$-$C_8$ heterocycloalkyl, —(CR'₅R'₆)ₘ—OR'₃, (CR'₅R'₆)ₘ(O)COR'₃, —CO(O)R'₃, —CONR'₃R'₄, —NR'₃R'₄, NR'₃(C(O)R'₄), or CH₂A when a compound of formula (1) is "A", wherein R'₃ and R'₄ are each independently hydrogen, $C_4$-$C_6$ alkyl, $C_3$-$C_8$ cycloalkyl, $C_4$-$C_{10}$ aryl, —(CR'₅R'₆)ₘ—$C_4$-$C_{10}$ aryl, —(CR'₅R'₆)ₘ—$C_4$-$C_{10}$ aryloxy, —(CR'₅R'₆)ₘ—$C_1$-$C_{10}$ heteroaryl, or —CO(O)R"₃, or R'₃ and R'₄ may form a cyclic structure of $C_2$-$C_{10}$ heterocycloalkyl or a cyclic structure of $C_4$-$C_{10}$ heteroaryl by mutual coupling, and R'₅ and R'₆ are each independently hydrogen or $C_1$-$C_3$ alkyl, wherein R"₃ is $C_1$-$C_6$ alkyl.

In addition, specific examples of the compound of Formula 1 are as follows.

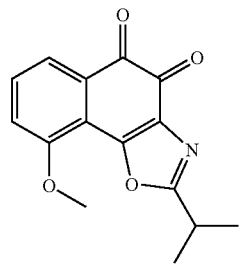

Compound 105

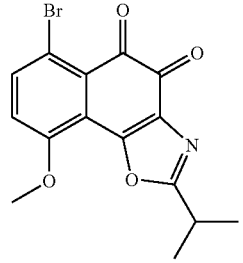

Compound 106

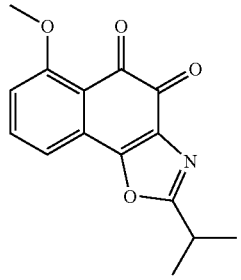

Compound 107

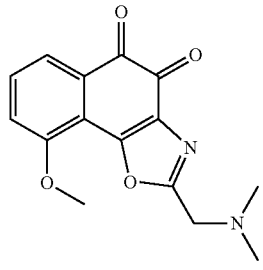

Compound 108

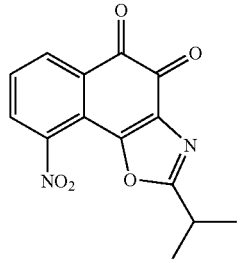

Compound 109

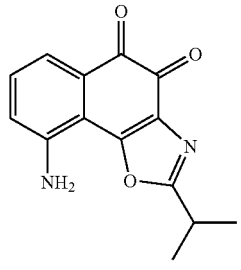

Compound 110

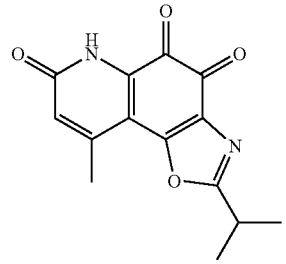

Compound 111

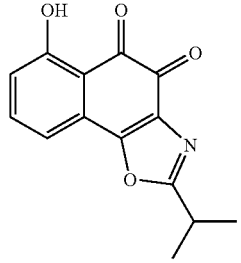

Compound 112

Compound 113
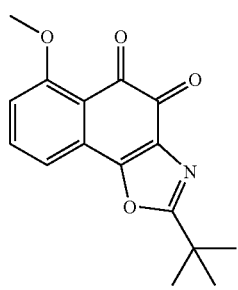
Compound 114
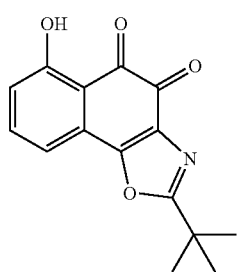
Compound 115
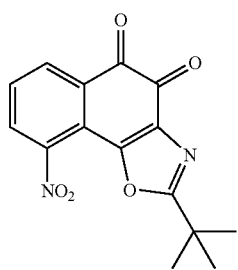
Compound 116
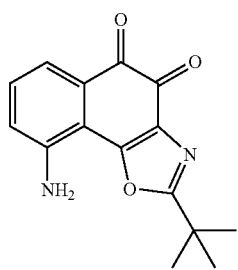
Compound 117
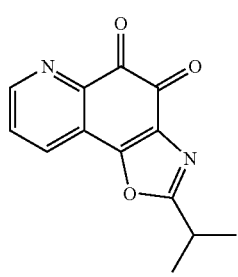
Compound 118
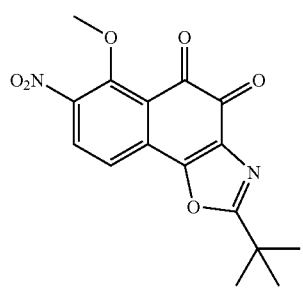
Compound 119
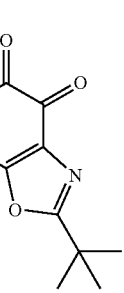
Compound 120
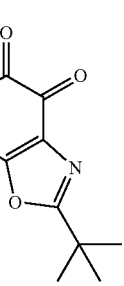
Compound 121
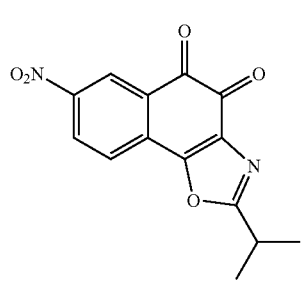
Compound 122
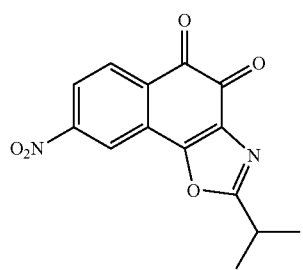

Compound 123
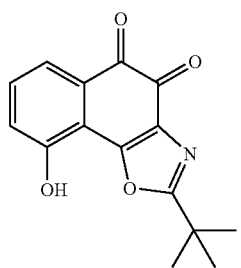
Compound 124
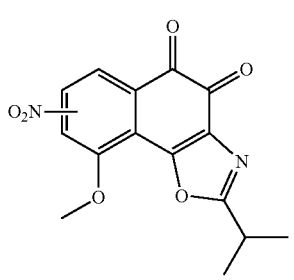
Compound 125
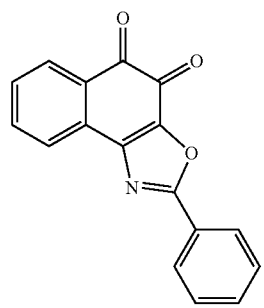
Compound 126
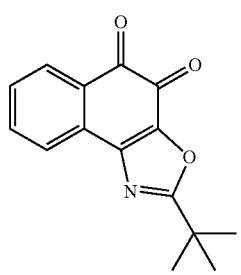
Compound 127
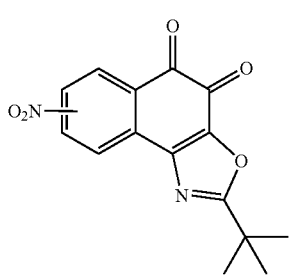
Compound 128
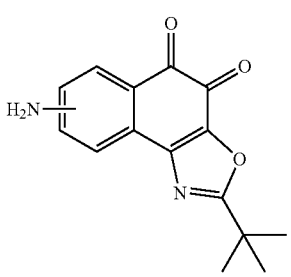
Compound 129
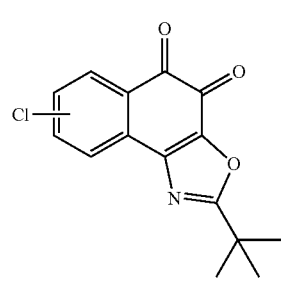
Compound 130
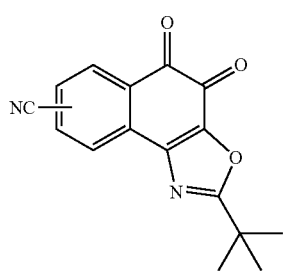
Compound 131
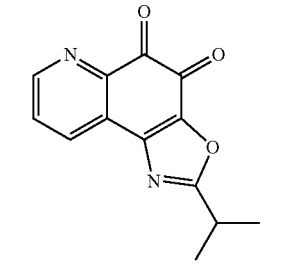
Compound 132
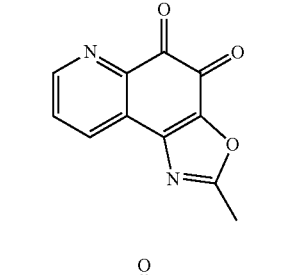
Compound 133

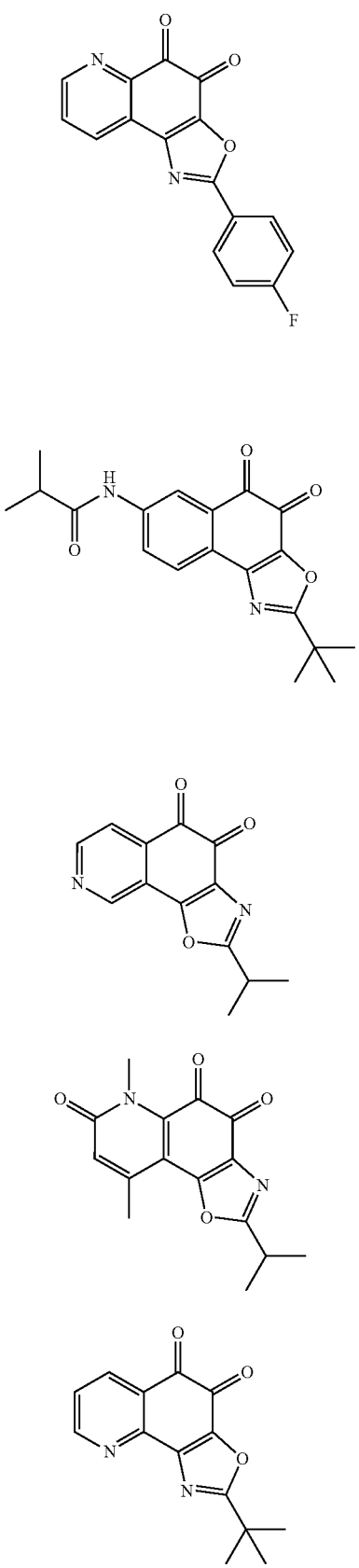

Compound 162
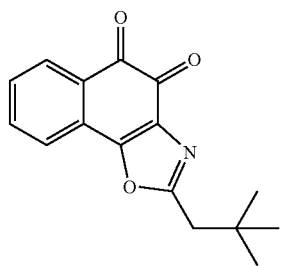
Compound 163
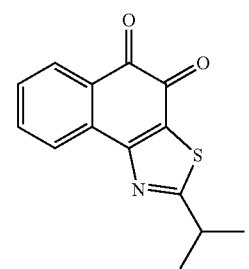
Compound 164
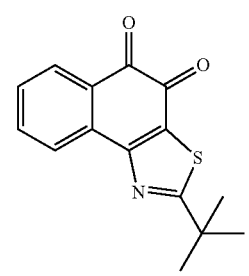
Compound 165
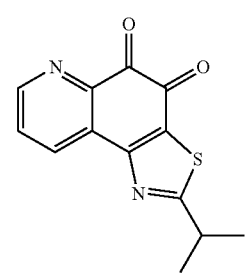
Compound 166
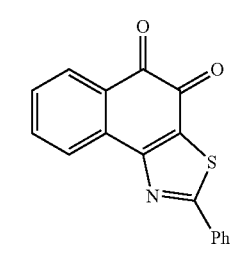
Compound 167
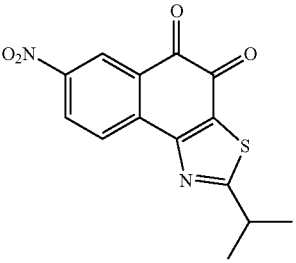
Compound 168
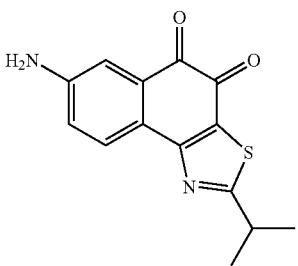
Compound 169
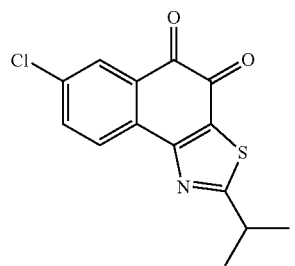
Compound 170
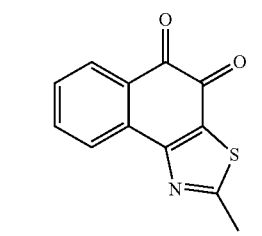
Compound 171
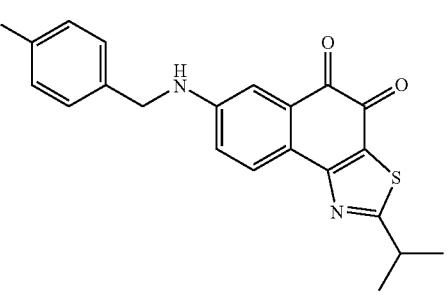
Compound 172
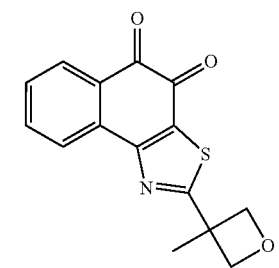

Compound 173
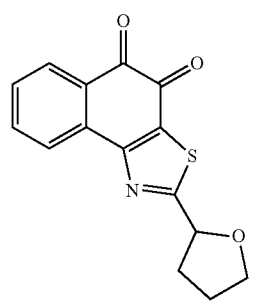
Compound 174
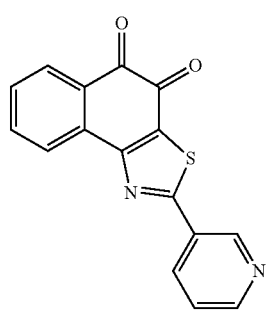
Compound 191
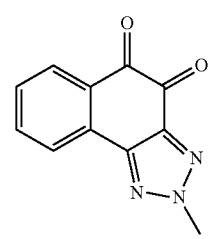
Compound 192
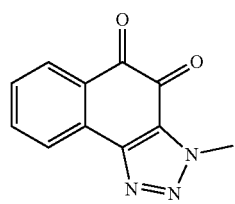
Compound 193
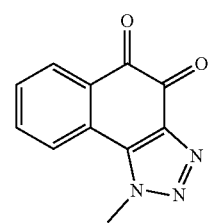
Compound 194
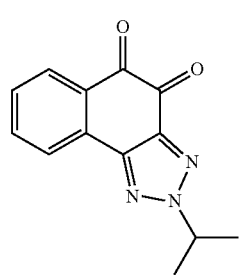
Compound 195
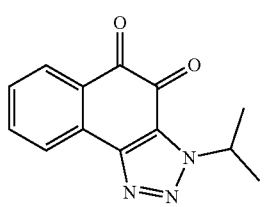
Compound 196
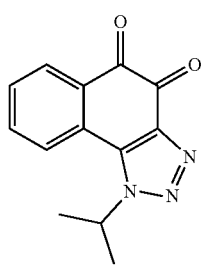
Compound 197
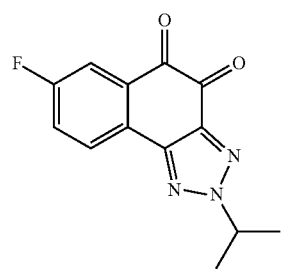
Compound 198
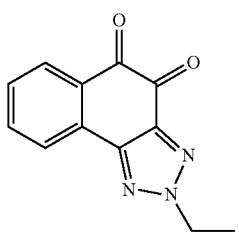
Compound 199
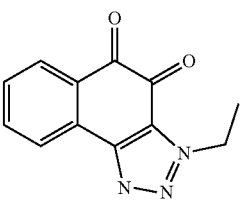
Compound 200
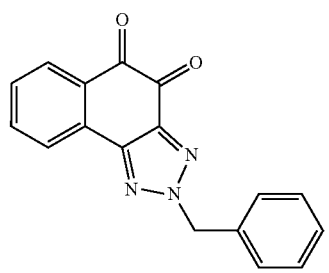

Compound 201
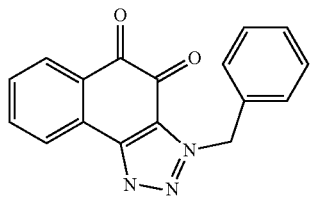
Compound 202
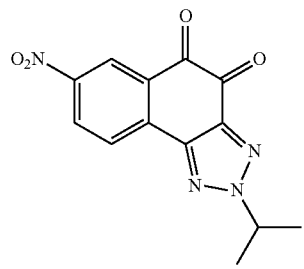
Compound 203
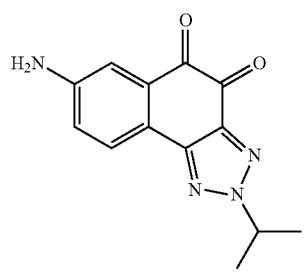
Compound 204
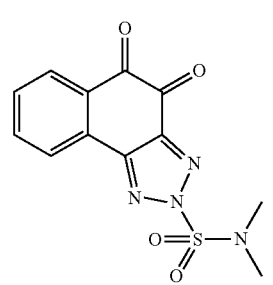
Compound 205
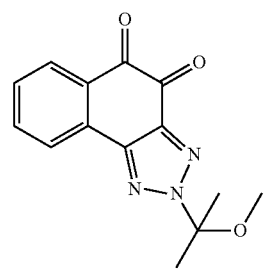
Compound 206
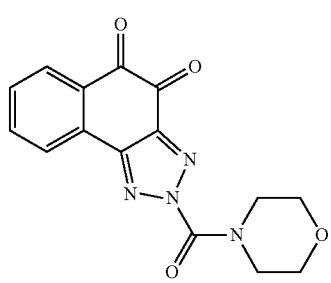
Compound 207
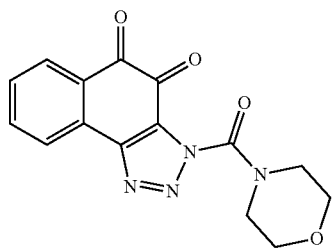
Compound 208
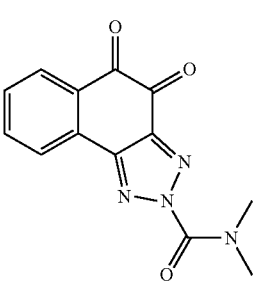
Compound 209
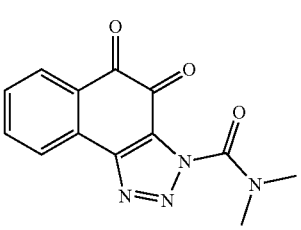
Compound 210
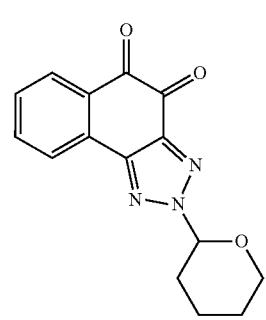
Compound 211
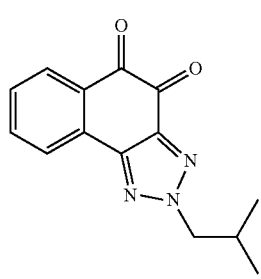
Compound 212
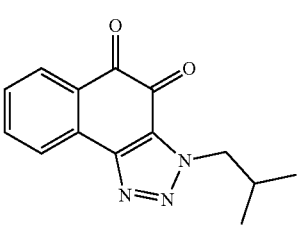

Compound 213
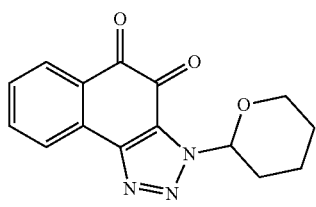
Compound 214
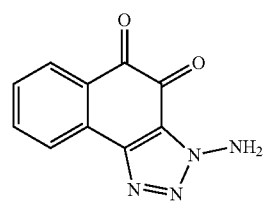
Compound 215
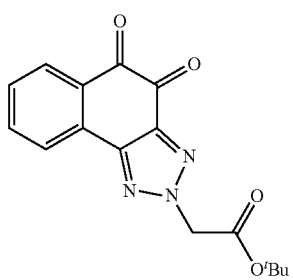
Compound 216
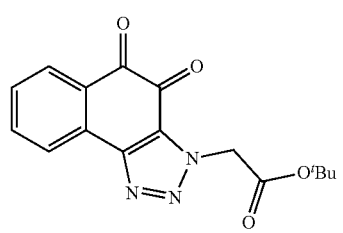
Compound 217
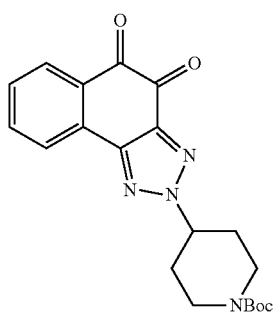
Compound 218
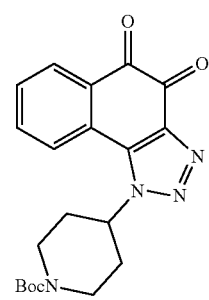
Compound 219
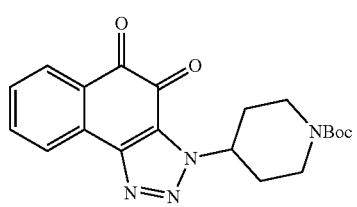
Compound 220
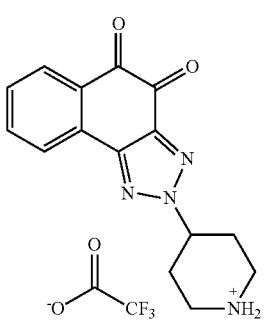
Compound 221
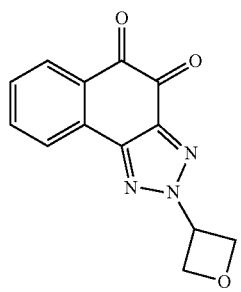
Compoound 222
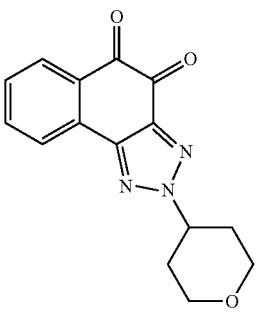
Compound 223
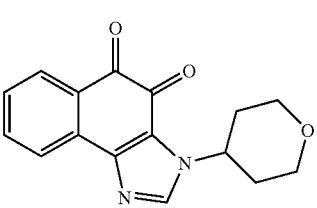

-continued
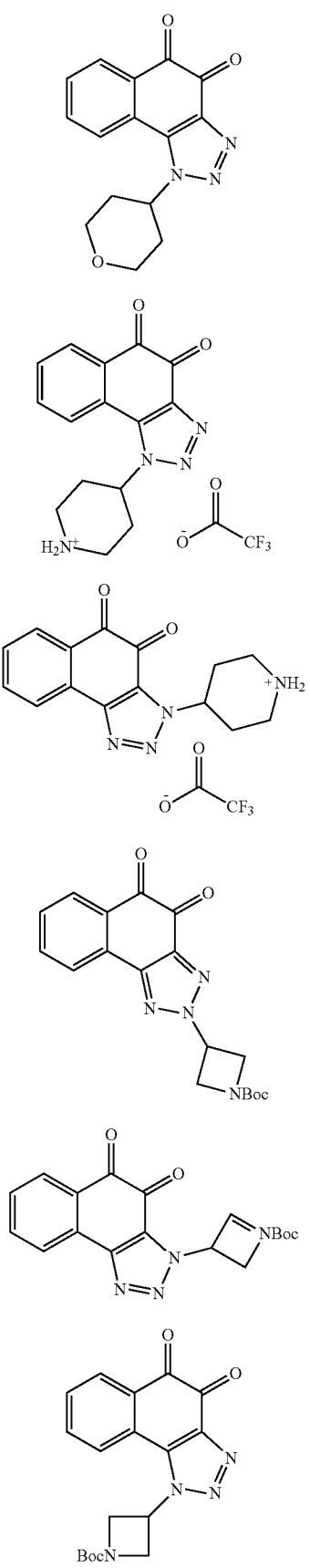
Compound 224
Compound 225
Compound 226
Compound 227
Compound 228
Compound 229
-continued
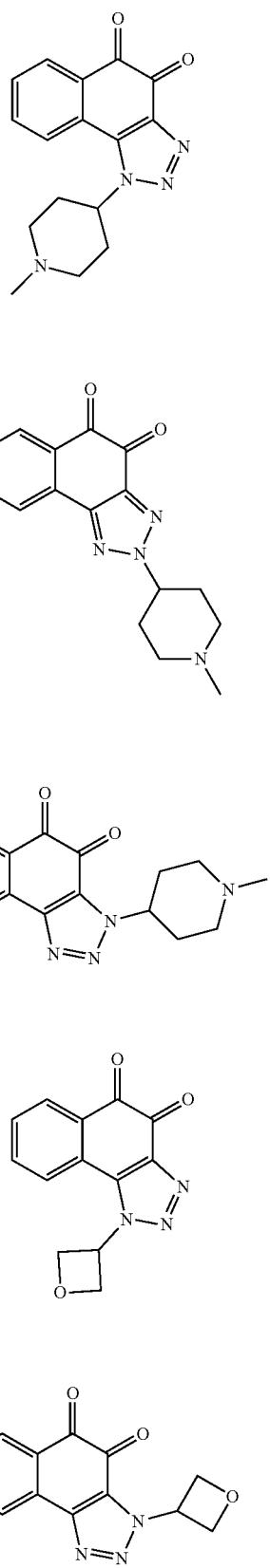
Compound 230
Compound 231
Compound 232
Compound 233
Compound 234
In addition, the compound may be one of the compounds expressed below.

Compound 151
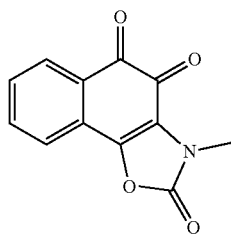
Compound 152
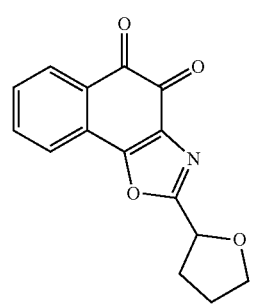
Compound 153
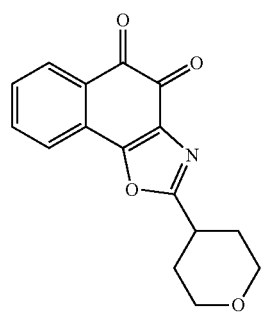
Compound 154
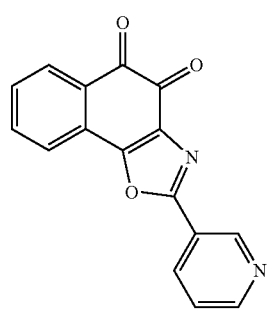
Compound 155
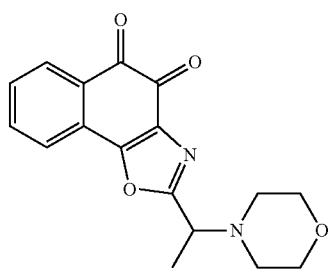
Compound 156
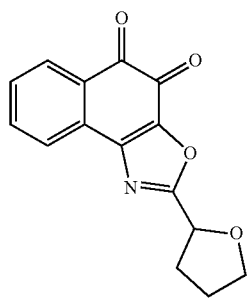
Compound 157
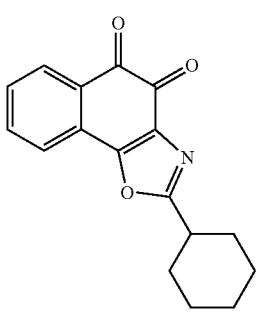
Compound 158
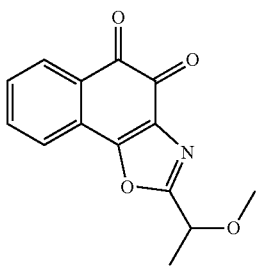
Compound 159
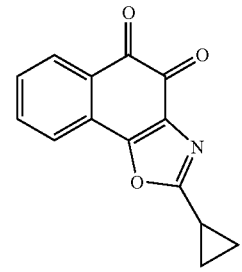
Compound 160
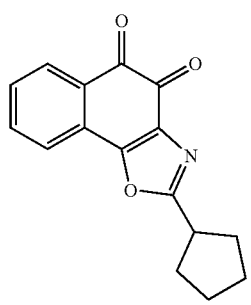

Compound 161

Compound 172

Compound 173

Compound 174

Compoound 230

Compound 231

Compound 232

Compound 233

Compound 234

Herein, the solid cancer may be at least one cancer selected from the group consisting of stomach cancer, liver cancer, colon cancer, breast cancer, lung cancer, non-small cell lung cancer, pancreatic cancer, skin cancer, head and neck cancer, uterine cancer, ovarian cancer, large intestine cancer, small intestine cancer, rectal cancer, prostate cancer, esophageal cancer, lymph gland cancer, bladder cancer, gallbladder cancer, kidney cancer, and brain tumor and, preferably, the cancer may be at least one cancer selected from the group consisting of lung cancer, uterine cancer, liver cancer, and breast cancer.

The acute leukemia in the blood cancer may be at least one cancer selected from the group consisting of acute myeloid leukemia and acute lymphoblastic leukemia.

The chronic leukemia in the blood cancer may be at least one cancer selected from the group consisting of chronic myeloid leukemia and chronic lymphocytic leukemia.

The blood cancer is drug-resistant leukemia having resistance to an existing anticancer drug, or refractory leukemia. Specifically, such a drug-resistant or refractory leukemia may be drug-resistant, refractory acute leukemia having resistance to idarubicin or cytarabine, which is a medicine for acute leukemia, or a drug-resistant, chronic leukemia having resistance to imatinib, which is a medicine for chronic leukemia.

Examples of the pharmaceutically acceptable salt of the 1,2-naphthoquinone derivative compound of the present disclosure may include: an addition salt formed by an inorganic acid, such as hydrochloride, sulfate, phosphate, hydrobromide, hydroiodide, nitrate, pyrosulfate, and metaphosphate; an addition salt formed by an organic acid, such as citrate, oxalate, benzoate, acetate, trifluoroacetate, propionate, succinate, fumarate, lactate, maleate, tartrate, glutarate, sulfonate; and a metal salt, such as a lithium salt, a sodium salt, a potassium salt, a magnesium salt, and a calcium salt, but are not limited thereto.

The pharmaceutical composition according to the present disclosure may be formulated into a suitable form together with a pharmaceutically acceptable carrier that is ordinarily used. The term "pharmaceutically acceptable" composition refers to a composition that is physiologically acceptable and does not cause allergic responses, such as gastrointestinal disorder or dizziness, or similar responses, when administered to humans. The composition may be formulated in the form of: an oral dosage form, such as a powder, granules, a tablet, a capsule, a suspension, an emulsion, a syrup, or an aerosol; a preparation for external application; a suppository; and a sterile injectable solution, according to usual methods, respectively.

Examples of the carrier, excipient, and diluent that may be contained in the composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl parahydroxybenzoate, propyl parahydroxybenzoate, talc, magnesium stearate, and a mineral oil, but are not limited thereto. The composition may be formulated into a preparation by using a diluent or an excipient, such as a filler, a stabilizer, a binder, a disintegrant, or a surfactant. A solid preparation for oral administration includes a tablet, a pill, a powder, granules, a capsule, and the like. Such solid preparations may be prepared by mixing the compound of the present disclosure with at least one excipient, for example, starch, microcrystal cellulose, sucrose or lactose, low-substituted hydroxypropyl cellulose, hypromellose, or the like. Alternatively, lubricants, such as magnesium stearate and talc, may be used in addition to the simple excipients. A liquid preparation for oral administration corresponds to a suspension, a liquid for internal use, an emulsion, a syrup, and the like, and may include simple diluents that are frequently used, such as water and liquid paraffin, and several types of excipients, for example, a wetting agent, a sweetener, an aroma, and a preservative. A preparation for parenteral administration includes a sterile aqueous solution, a non-aqueous solvent, a suspension, an emulsion, a lyophilizer, and a suppository. The non-aqueous solvent and the suspension solvent may include propylene glycol, polyethylene glycol, a vegetable oil, such as olive oil, an injectable ester, such as ethylolate, and the like. As a substrate for the suppository, Witepsol, Macrogol, Tween 61, cacao butter, laurin butter, glycerol, gelatin, or the like may be used. For the formulation into a dosage form for parenteral administration, the 1,2-naphthoquinone derivative compound of Formula 1 or the pharmaceutically acceptable salt thereof may be sterilized and/or mixed with a preservative, a stabilizer, a hydrator, an emulsion promoter, a salt for osmotic pressure regulation, and/or an adjurvant, such as a buffer, and other therapeutically useful substances in water to be made into a solution or a suspension, which is then prepared into an ampule or vial unit dosage form.

The pharmaceutical composition containing the compound of Formula 1 as an active ingredient, disclosed in the present disclosure, may be administered to mammalian animals, such as mice, livestock, and humans, via various routes to prevent or treat solid cancer or blood cancer. All manners of administration may be predicted, and for example, the administration may be carried out through oral, rectal, intravenous, intramuscular, subcutaneous, intrauterine dural, intracerebroventricular injection. The dose may vary depending on the age, sex, or body weight of a subject to be treated, the particular disease or pathological condition to be treated, the severity of the disease or pathological condition, the time of administration, the route of administration, the absorption, distribution, and excretion rate of a drug, the kind of another drug used, and the determination of a prescriber. The determination of the dose on the basis of these factors is within the level of a person skilled in the art, and the usual dose is in a range of 0.01-2000 mg/kg/day. More preferably, the dose is 1-500 mg/kg/day. The dose may be administered once a day or divided into multiple doses. The dose is not intended to limit the scope of the present disclosure in any way.

Advantageous Effects

The present disclosure is directed to a pharmaceutical composition for preventing or treating solid cancer, or blood cancer, such as acute leukemia or chronic leukemia, the pharmaceutical composition containing a 1,2-naphthoquinone derivative compound or a pharmaceutically acceptable salt thereof as an active ingredient. The 1,2-naphthoquinone derivative compound, when used to treat solid cancer, acute and chronic leukemia, and drug-resistant/refractory leukemia cell lines, has an excellent cell-killing effect, and thus can be helpfully used in a pharmaceutical composition for preventing or treating the above cancer types.

MODE FOR CARRYING OUT THE INVENTION

Figure 1:
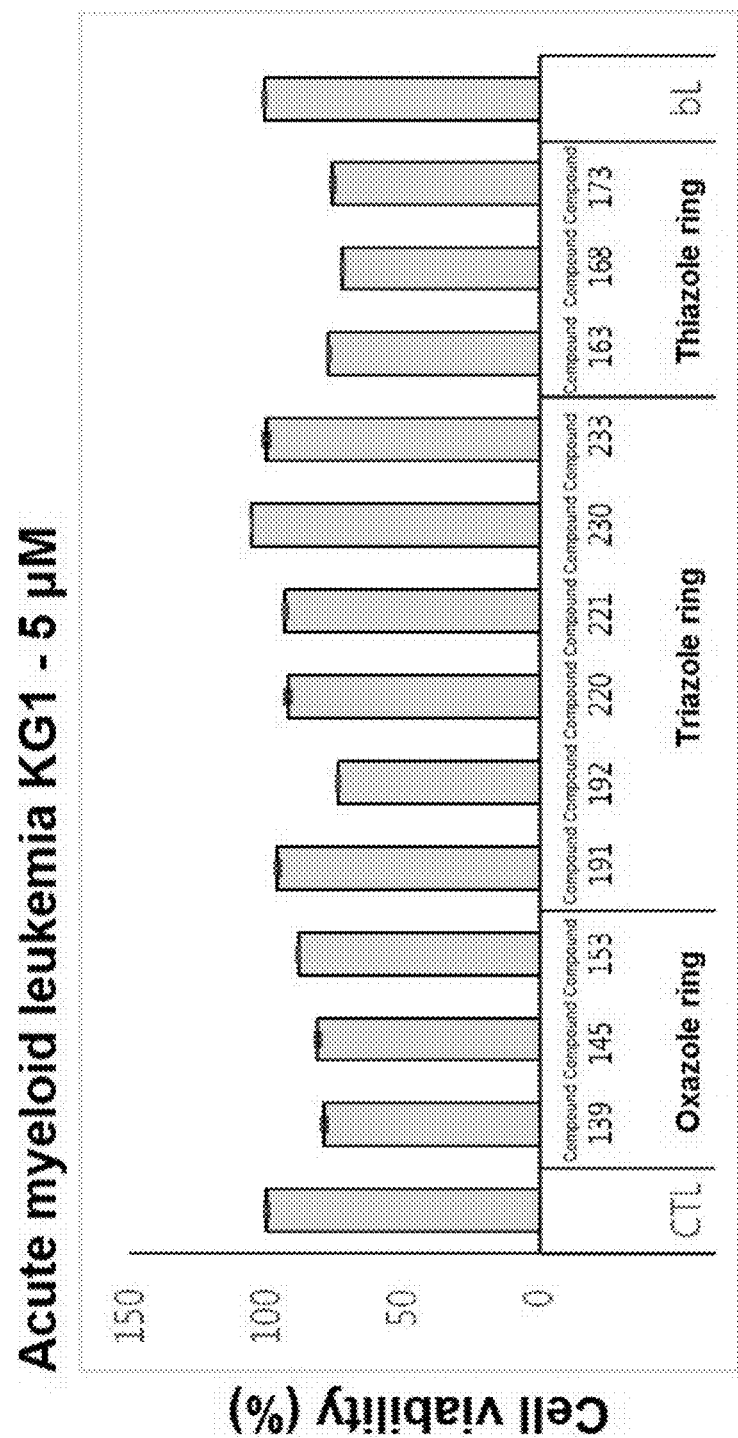
FIG. 1 is a graph showing cell viability of acute myeloid leukemia KG1 cells when the cells were treated with the compounds of the present disclosure.

Hereinafter, preferable embodiments of the present disclosure will be described in detail. However, the present disclosure is not limited to the embodiments described herein, and can be embodied in many different forms. Rather, these embodiments are provided so that this disclosure will be thorough and complete and will fully convey the scope of the disclosure to those skilled in the art.

Example 1: Synthesis of 1,2-Naphthoquinone Derivative Compounds

As for a 1,2-naphthoquinone derivative compound of the present disclosure used to investigate the treatment effect on acute leukemia, chronic leukemia, and solid cancer, compounds 99-174 and 191-234 were synthesized with reference to the compound synthesis methods disclosed in Korean Patent Application Nos. 10-2014-0193184, 10-2014-0193306, 10-2014-0193370, 10-2015-0043050, and 10-2015-0043068. Out of the compounds prepared through the above procedures, physicochemical characteristics of compounds 151-161, 172-174, and 230-234 are shown in Tables 1 to 3.

TABLE 1

| Compound No. | $^1$H NMR data |
|---|---|
| 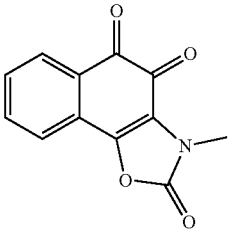<br>Compound 151 | $^1$H NMR (300 MHz, CDCl$_3$) δ 8.17-8.09 (m, 2H), 7.82-7.74 (m, 2H), 3.68 (s, 3H) |
| 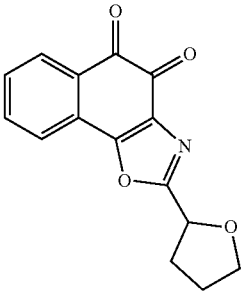<br>Compound 152 | $^1$H NMR (300 MHz, CDCl$_3$) δ 8.16 (d, J = 7.8 Hz, 1H), 7.78-7.69 (m, 2H), 7.57 (t, J = 7.5 Hz, 1H), 5.19-5.15 (m, 1H), 4.13-3.97 (m, 2H), 2.58-2.34 (m, 2H), 2.27-2.01 (m, 2H) |

TABLE 1-continued

| Compound No. | $^1$H NMR data |
|---|---|
| 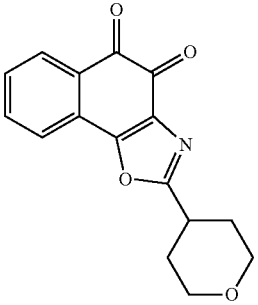<br>Compound 153 | $^1$H NMR (300 MHz, CDCl$_3$) δ 8.15 (d, J = 7.5 Hz, 1H), 7.75-7.68 (m, 2H), 7.59-7.53 (m, 1H), 4.12-4.05 (m, 2H), 3.62-3.53 (m, 2H), 3.27-3.17 (m, 1H), 2.15-1.98 (m, 4H) |
| 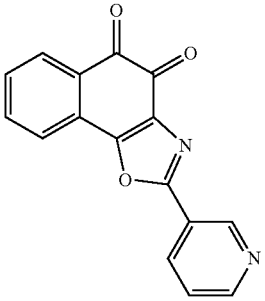<br>Compound 154 | $^1$H NMR (300 MHz, DMSO) δ 9.36 (s, 1H), 8.81 (d, J = 6.3 Hz, 1H), 8.53 (d, J = 8.1 Hz, 1H), 8.03 (d, J = 7.8 Hz, 1H), 7.99 (d, J = 7.8 Hz, 1H), 7.83 (t, J = 7.5 Hz, 1H), 7.69-7.62 (m, 2H) |
| 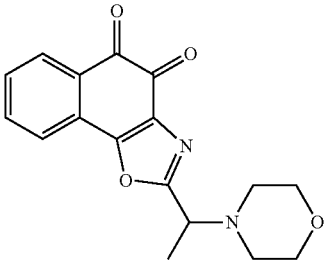<br>Compound 155 | $^1$H NMR (300 MHz, CDCl$_3$) δ 8.16 (d, J = 7.8 Hz, 1H), 7.76-7.69 (m, 2H), 7.58 (t, J = 7.2 Hz, 1H), 4.08-4.01 (m, 1H), 3.74-3.71 (m, 4H), 2.72-2.55 (m, 4H), 1.60 (d, J = 7.2 Hz, 3H) |
| 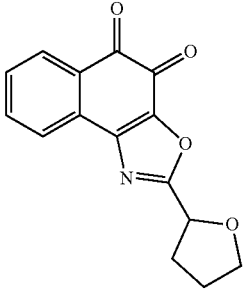<br>Compound 156 | $^1$H NMR (300 MHz, CDCl$_3$) δ 8.13 (d, J = 7.8 Hz, 1H), 7.99 (d, J = 7.5 Hz, 1H), 7.70 (t, J = 7.5 Hz, 1H), 7.53 (t, J = 7.5 Hz, 1H), 5.22-5.17 (m, 1H), 4.21-4.13 (m, 1H), 4.08-4.00 (m, 1H), 2.53-2.05 (m, 4H) |

TABLE 2

| Compound No. | | ¹H NMR data |
|---|---|---|
| Compound 157 | 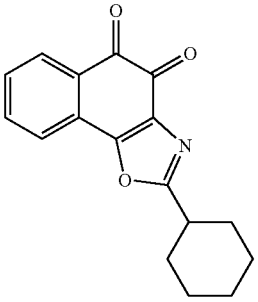 | ¹H NMR (300 MHz, CDCl₃) δ 8.13 (d, J = 7.5 Hz, 1H), 7.73-7.67 (m, 2H), 7.57-7.49 (m, 1H), 2.99-2.89 (m, 1H), 2.19-2.13 (m, 2H), 1.91-1.85 (m, 2H), 1.76-1.59 (m, 3H), 1.49-1.24 (m, 3H) |
| Compound 158 | 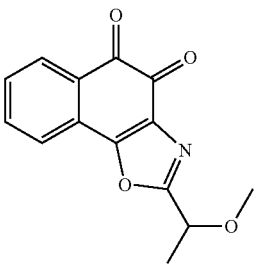 | ¹H NMR (300 MHz, CDCl₃) δ 8.17 (d, J = 7.8 Hz, 1H), 7.78-7.74 (m, 2H), 7.59 (t, J = 6.9 Hz, 1H), 4.65-4.62 (m, 1H), 3.44 (s, 3H), 1.69 (t, J = 6.6 Hz, 3H) |
| Compound 159 | 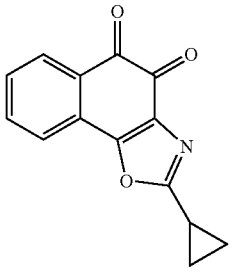 | ¹H NMR (300 MHz, CDCl₃) δ 8.13 (d, J = 7.5 Hz, 1H), 7.71-7.64 (m, 2H), 7.52 (t, J = 7.8 Hz, 1H), 2.22-2.16 (m, 1H), 1.32-1.18 (m, 4H) |
| Compound 160 | 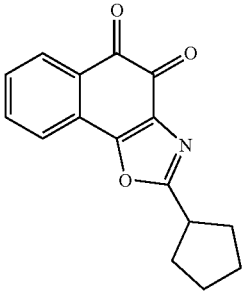 | ¹H NMR (300 MHz, CDCl₃) δ 8.14-8.11 (m, 1H), 7.80-7.71 (m, 2H), 7.65-7.50 (m, 1H), 3.38-3.33 (m, 1H), 2.62-2.00 (m, 4H), 2.00-1.25 (m, 4H) |

TABLE 2-continued

| Compound No. | | ¹H NMR data |
|---|---|---|
| Compound 161 | 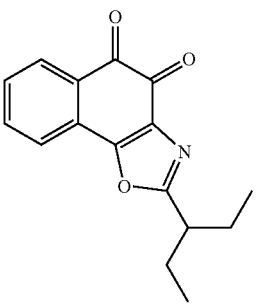 | ¹H NMR (300 MHz, CDCl₃) δ 8.24-8.13 (m, 1H), 7.73-7.68 (m, 2H), 7.59-7.53 (m, 1H), 2.96-2.88 (m, 1H), 2.70-2.65 (m, 4H), 1.65-1.51 (m, 6H) |
| Compound 172 | 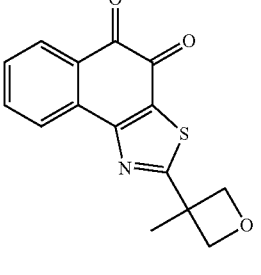 | ¹H NMR (300 MHz, CDCl₃) δ 8.21 (d, J = 6.6 Hz, 1H), 8.16 (d, J = 6.6 Hz, 1H), 7.76 (t, J = 7.8 Hz, 1H), 7.57 (t, J = 7.8 Hz, 1H), 4.52 (d, J = 12.6 Hz, 1H), 4.23 (d, J = 12.3 Hz, 1H), 3.82 (d, J = 12.3 Hz, 1H), 3.68 (d, J = 12.9 Hz, 1H), 3.45 (s, 3H) |
| Compound 173 | 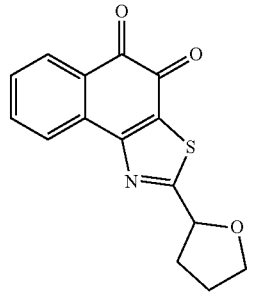 | ¹H NMR (300 MHz, CDCl₃) δ 8.15 (d, J = 7.8 Hz, 1H), 8.11 (d, J = 7.5 Hz, 1H), 7.70 (t, J = 7.5 Hz, 1H), 7.50 (t, J = 7.8 Hz, 1H), 5.31-5.27 (m, 1H), 4.21-4.13 (m, 1H), 4.10-3.97 (m, 1H), 2.61-2.49 (m, 1H), 2.29-2.19 (m, 1H), 2.11-1.96 (m, 2H) |

TABLE 3

| Compound No. | | ¹H NMR data |
|---|---|---|
| Compound 174 | 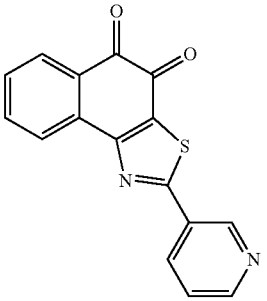 | ¹H NMR (300 MHz, CDCl₃) δ 9.37 (s, 1H), 8.81 (d, J = 4.8 Hz, 1H), 8.41-8.34 (m, 2H), 8.19 (d, J = 7.8 Hz, 1H), 7.79 (t, J = 7.5 Hz, 1H), 7.58 (t, J = 7.5 Hz, 1H), 7.53-7.49 (m, 1H) |

TABLE 3-continued

| Compound No. | ¹H NMR data |
|---|---|
| 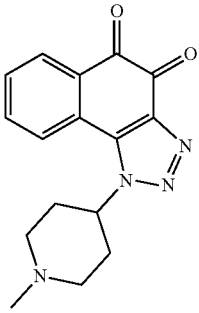  Compound 230 | ¹H NMR (300 MHz, CDCl₃) δ 8.32 (d, J = 7.8 Hz, 1H), 7.81-7.74 (m, 2H), 7.65 (t, J = 7.5 Hz, 1H), 4.76-4.67 (m, 1H), 3.14-3.10 (m, 2H), 2.62-2.54 (m, 2H), 2.41 (s, 3H), 2.33-2.25 (m, 4H) |
| 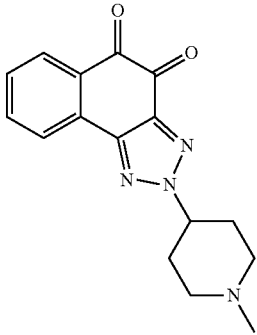  Compound 231 | ¹H NMR (300 MHz, CDCl₃) δ 8.19 (d, J = 7.8 Hz, 1H), 8.00 (d, J = 7.8 Hz, 1H), 7.73 (t, J = 7.8 Hz, 1H), 7.53 (t, J = 7.8 Hz, 1H), 4.63-4.56 (m, 1H), 3.01-2.97 (m, 2H), 2.40-2.18 (m, 9H) |
| 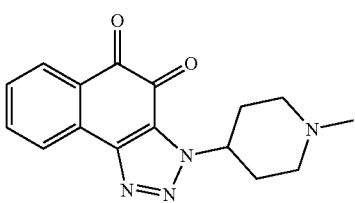  Compound 232 | ¹H NMR (300 MHz, CDCl₃) δ 8.21 (d, J = 7.8 Hz, 1H), 8.13 (d, J = 7.8 Hz, 1H), 7.74 (t, J = 7.8 Hz, 1H), 7.52 (t, J = 7.8 Hz, 1H), 4.99-4.92 (m, 1H), 3.06-3.02 (m, 2H), 2.46-2.17 (m, 9H) |
| 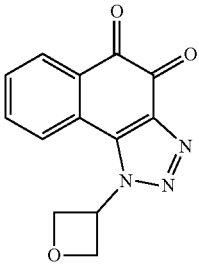  Compound 233 | ¹H NMR (300 MHz, CDCl₃) δ 8.28 (d, J = 5.7 Hz, 1H), 7.82 (t, J = 7.5 Hz, 1H), 7.68 (t, J = 7.8 Hz, 1H), 7.57 (d, J = 7.2 Hz, 1H), 6.16-6.12 (m, 1H), 5.43 (t, J = 6.0 Hz, 2H), 5.30 (t, J = 6.9 Hz, 2H) |
| 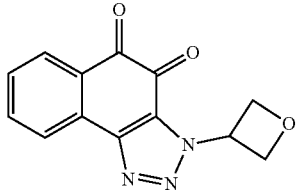  Compound 234 | ¹H NMR (300 MHz, CDCl₃) δ 8.23 (d, J = 7.5 Hz, 1H), 8.14 (d, J = 7.8 Hz, 1H), 7.77 (t, J = 7.5 Hz, 1H), 7.55 (t, J = 7.8 Hz, 1H), 6.18-6.09 (m, 1H), 5.29-5.17 (m, 4H) |

Example 2: Preparation of Acute Leukemia Cell Lines and Measurement of Cell Viability Thereof Example 2-1: Preparation of Acute Leukemia Cell Lines Acute leukemia has been identified to have a wide variety of causative factors and a variety of cell lines have also been established. To investigate the availability as a wide-spectrum medicine but not a medicine for a particular type of acute leukemia, KG1α cells were constructed by selecting only cells having a stem cell phenotype from KG1 cells, which are a cell line obtained from a 59-year-old-male with acute myeloid leukemia, and then used.

KG1α cells were incubated in IMDM containing 20% fetal bovine serum (FBS). All the cells were incubated at 37□ in a 5% CO₂ incubator, and subcultured every 2 or 3 days before use in the test.

Example 2-2: Measurement of Cell Viability of KG1α Cells-WST Assay

KG1α cells, which have resistance to idarubicin and cytarabine, which are acute myeloid leukemia medicines, are refractory acute myeloid leukemia (AML) cells. KG1α cells incubated in Example 2-1 were seeded at 1×10⁵ cells/well in a 96-well plate, and then for cell stabilization, the cells were incubated at 37□ in a 5% CO₂ incubator for 16 hours or longer. Thereafter, the cells were treated with compounds 99 and 163 (0.1-3 μM) shown in Table 4 out of the compounds synthesized in Example 1, and then incubated for 24 hours. Here, DMSO was used as a control (hereinafter, also referred to as "CTL"; see drawings). After 24 hours, the cells were treated with 10 μl of WST solution and then incubated for 2 hours, and then the absorbance at 450 nm was measured by a multi-scan machine. The cell viability of KG1α cells are shown in Table 4.

TABLE 4

| Condition | IC₅₀ (μM) |
|---|---|
| 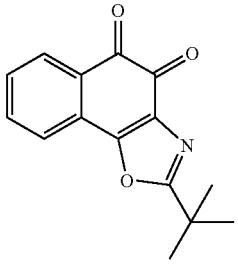  Compound 99 | 1.2 |
| 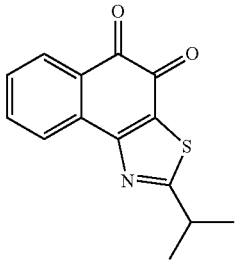  Compound 163 | 0.9 |

Table 4 shows the cell viability of KG1α cells treated with compounds 99 and 163 of the present disclosure compared with the control, and confirmed that the compounds showed an $IC_{50}$ value of 0.5-1 μM, indicating an excellent effect of killing acute myeloid leukemia cells.

Example 2-3: Measurement of Cell Viability of KG1α Cells—CCK-8 Assay

To measure the cell viability of KG1α cells by CCK-8 assay, which is a method for quantifying cell counts through responses in mitochondria, KG1 cells, which are acute myeloid leukemia cells, and KG1α cells, which were constructed by selecting only cells having a stem cell phenotype from the KG1 cells, were used.

KG1α and KG1 cells were incubated in IMDM containing 20% fetal bovine serum (FBS). All the cells were incubated at 37□ in a 5% $CO_2$ incubator and subcultured every 2 or 3 days before use in the test.

KG1 cells and KG1α cells were incubated at 2×10⁵ cells/well in 96-well plates, and then were treated for 12 hours with the compounds of the present disclosure, which were dissolved in DMSO and diluted at a ratio of 1/2000 to a final concentration of 5 μM. Thereafter, CCK-8 drug (Dojindo Molecular Technologies, Inc., MD, USA) was added at 10 μl per well. After 30 minutes, the absorbance was measured using 450-nm and 595-nm filters by the microreader, MultiSkan Ascent microplate spectrophotometer (Thermo Fisher Scientific, Inc.).

A group treated with only DMSO is used as a control. On the basis of when the result of the control was considered to be 100%, the cell viability according to the treatment with the compounds of the present disclosure was identified, and the results are shown in FIGS. 1 and 2.

Figure 2:
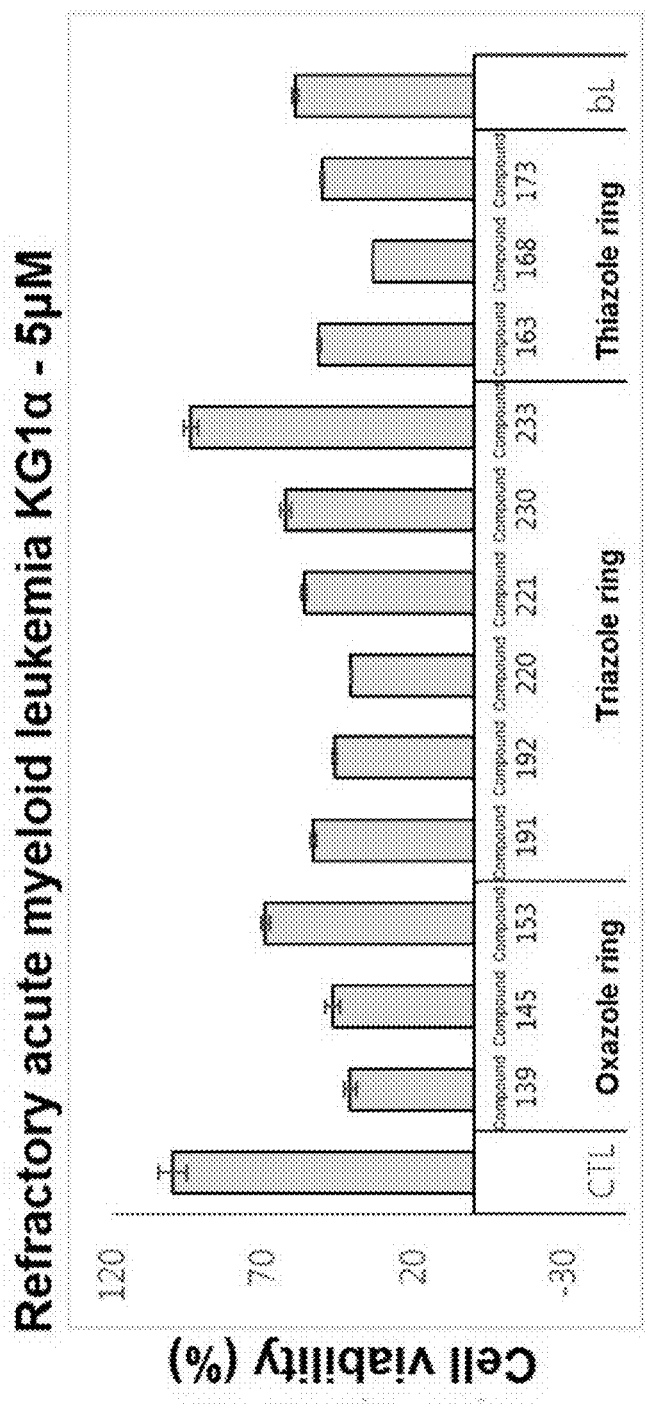
FIG. 2 is a graph showing cell viability of refractory acute myeloid leukemia KG1α cells when the cells were treated with the compounds of the present disclosure.

As can be seen from FIGS. 1 and 2, compared with previously known β-lapachone, the compounds of the present disclosure showed an excellent anticancer effect on acute myeloid leukemia cells, and especially, showed a very excellent effect on KG1α cells, which are refractory acute myeloid leukemia (AML) cells.

Example 3: Preparation of Chronic Leukemia Cell Lines and Measurement of Cell Viability Thereof

Example 3-1: Preparation of Acute Leukemia Cell Line

K562 cells obtained from a 53-year-old-female with chronic myeloid leukemia were incubated in RPMI medium containing 10% fetal bovine serum (FBS) at 37□ in a 5% CO2 incubator, and subcultured every 2 days before use in the test.

Example 3-2: Measurement of Cell Viability in Chronic Leukemia Cells—WST Assay K562 cells incubated in Example 3-1 were seeded at 1×10⁵ cells/well in a 96-well plate, and then for cell stabilization, the cells were incubated at 37□ in a 5% $CO_2$ incubator for 16 hours or longer. Thereafter, the cells were treated with compounds 99, 163, 191, and 192 (0.1-5 μM) out of the compounds synthesized in Example 1-1, and then incubated for 4 hours. DMSO was used as a control. After 4 hours of incubation, 10 μl of WST solution was added to the cells, followed by incubation for 2 hours, and then the absorbance at 450 nm was measured by a multi-scan machine. The cell viability of K562 cells are shown in Table 5.

TABLE 5

| Condition | $IC_{50}$ (μM) |
|---|---|
| Compound 99 | 1.7 |
| Compound 163 | 2.1 |
| Compound 191 | 1.6 |
| Compound 192 | 1.2 |

Referring to Table 5 above, it was confirmed that compared with the control, compounds 99, 163, 191, and 192 of the present disclosure, when were used to treat K562 cells, showed an $IC_{50}$ value of 1-2 μM, indicating an excellent effect of killing chronic myeloid leukemia cells.

Example 3-3: Measurement of Cell Viability of K562 and K562R Cells—CCK-8 Assay To measure the cell viability of chronic myeloid leukemia cells by CCK-8 assay, which is a method for quantifying cell counts through responses in mitochondria, K562 cells, which are chronic myeloid leukemia cells, and K562R cells, which are a cell line having imatinib resistance by incubation in a medium containing 1 µM imatinib, were used. K562 cells and K562R cells were incubated in RPMI medium containing 10% fetal bovine serum (FBS) at 37° in a 5% $CO_2$ incubator, and subcultured every 2 days before use in the test.

The cells were incubated in 96-well plates at $2\times10^5$/well, and then were treated for 12 hours with the compounds of the present disclosure, which were dissolved in DMSO and diluted at a ratio of 1/2000 to a final concentration of 5 µM.

Thereafter, CCK-8 drug was added at 10 µl per well. After 30 minutes, the absorbance was measured using 450-nm and 595-nm filters by the microreader.

A group treated with only DMSO is used as a control. On the basis of when the result of the control was considered to be 100%, the cell viability according to the treatment with the compounds of the present disclosure was identified, and the results are shown in FIGS. 3 and 4.

Figure 3:
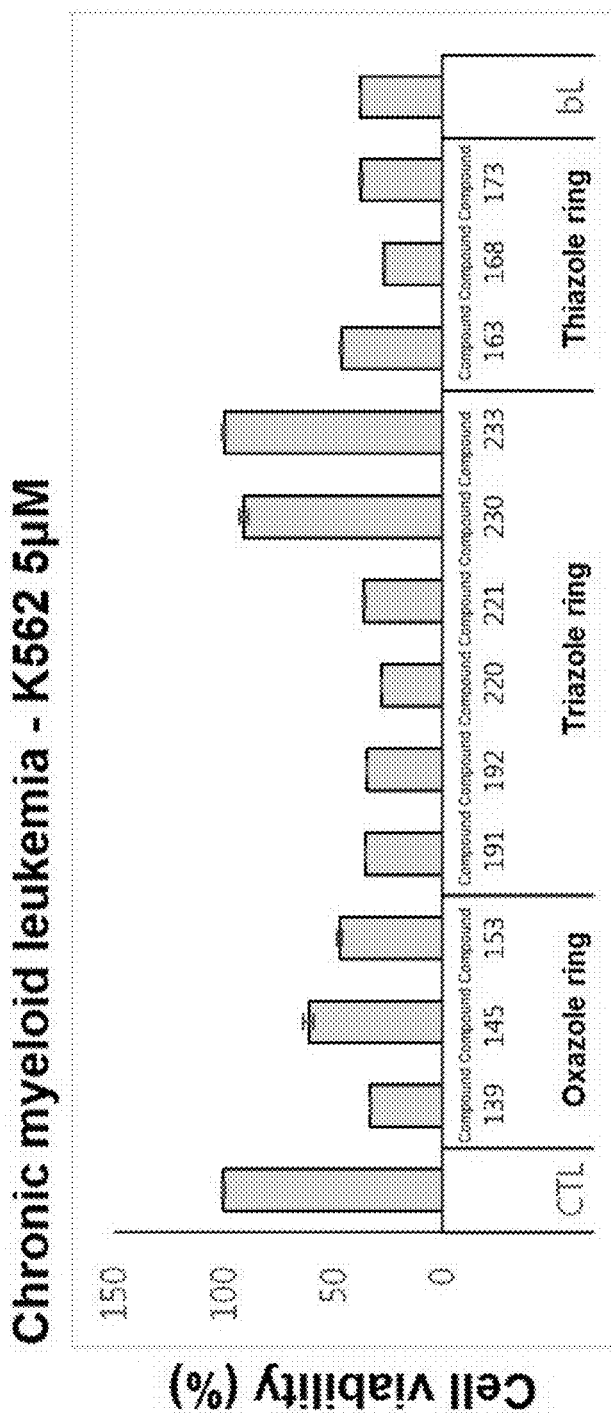
FIG. 3 is a graph showing cell viability of chronic myeloid leukemia K562 cells when the cells were treated with the compounds of the present disclosure.
Figure 4:
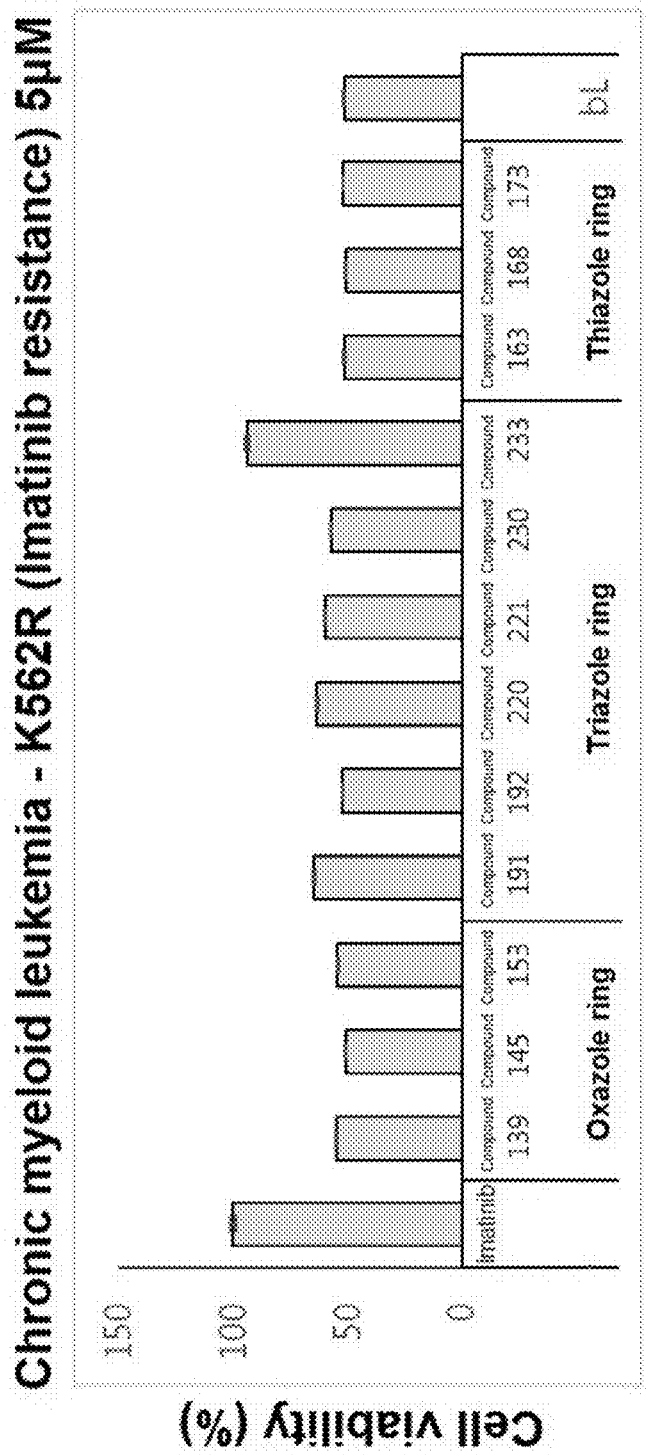
FIG. 4 is a graph showing cell viability of chronic myeloid leukemia imatinib-resistant K562R cells when the cells were treated with the compounds of the present disclosure.

As shown in FIGS. 3 and 4, compared with previously known β-lapachone, the compounds of the present disclosure showed an excellent viability inhibitory effect on not only K562 cells, which are chronic myeloid leukemia cells, but also K562R cell line, which has resistance to imatinib as a primary chronic leukemia medicine, indicating an excellent anticancer effect on chronic leukemia.

Example 4: Preparation of Solid Cancer Cell Lines and Measurement of Cell Viability Thereof Example 4-1: Preparation of Solid Cancer Cell Lines To investigate availability as a medicine for solid cancer, A549 cell line obtained from a 58-year-old-male with lung carcinoma, HeLa cell line obtained from a 31-year-old female with cervix adenocarcinoma, HepG2 cell line obtained from a 15-year-old boy with hepatocellular carcinoma, MCF7 cell line obtained from a 69-year-old female with breast adenocarcinoma, and Beas-2B cell line obtained from normal lung for comparison with solid cancer cell line were used.

A549 (lung carcinoma), HeLa (cervix adenocarcinoma), HepG2 (hepatocellular carcinoma), MCF7 (breast adenocarcinoma), and Beas-2B (normal lung) cell lines were incubated in DMEM medium containing 10% FBS at 37° in a 5% $CO_2$ incubator, and subcultured every 2 days before use in the test.

Example 4-2: Measurement of Cell Viability of Solid Cancer Cells—WST Assay

A549 (lung carcinoma), HeLa (cervix adenocarcinoma), HepG2 (hepatocellular carcinoma), MCF7 (breast adenocarcinoma), and Beas-2B (normal lung) cells were seeded at $1\times10^4$ cells/well in a 96-well plate, and then for cell stabilization, the cells were incubated at 37° in a 5% $CO_2$ incubator for 16 hours or longer. Thereafter, the cells were treated with compounds 99, 163, 191, and 192 (1-30 µM) out of the compounds synthesized in Example 1-1, and then incubated for 6 hours. DMSO and β-lapachone were used as a control. After 4 hours of incubation, 10 µl of WST solution was added to the cells, followed by incubation for 2 hours, and then the absorbance at 450 nm was measured by a multi-scan machine. The cell viability of A549 (lung carcinoma), HeLa (cervix adenocarcinoma), HepG2 (hepatocellular carcinoma), MCF7 (breast adenocarcinoma), and Beas-2B (normal lung) cells is shown in Table 5 and FIG. 5.

TABLE 6

| Condition | IC50 (µM) | | | |
| --- | --- | --- | --- | --- |
| | A549 | Hela | HepG2 | MCF7 |
| Positive control (β-lapachone) | 5.0 | 4.8 | 12.3 | 13.2 |
| Compound 99 | 9.2 | 4.5 | 15.4 | 12.9 |
| Compound 163 | 6.1 | 4.6 | 14.1 | 13.0 |
| Compound 191 | 8.4 | 6.6 | 13.8 | 14.8 |
| Compound 192 | 5.0 | 4.4 | 12.2 | 11.7 |

Figure 5:
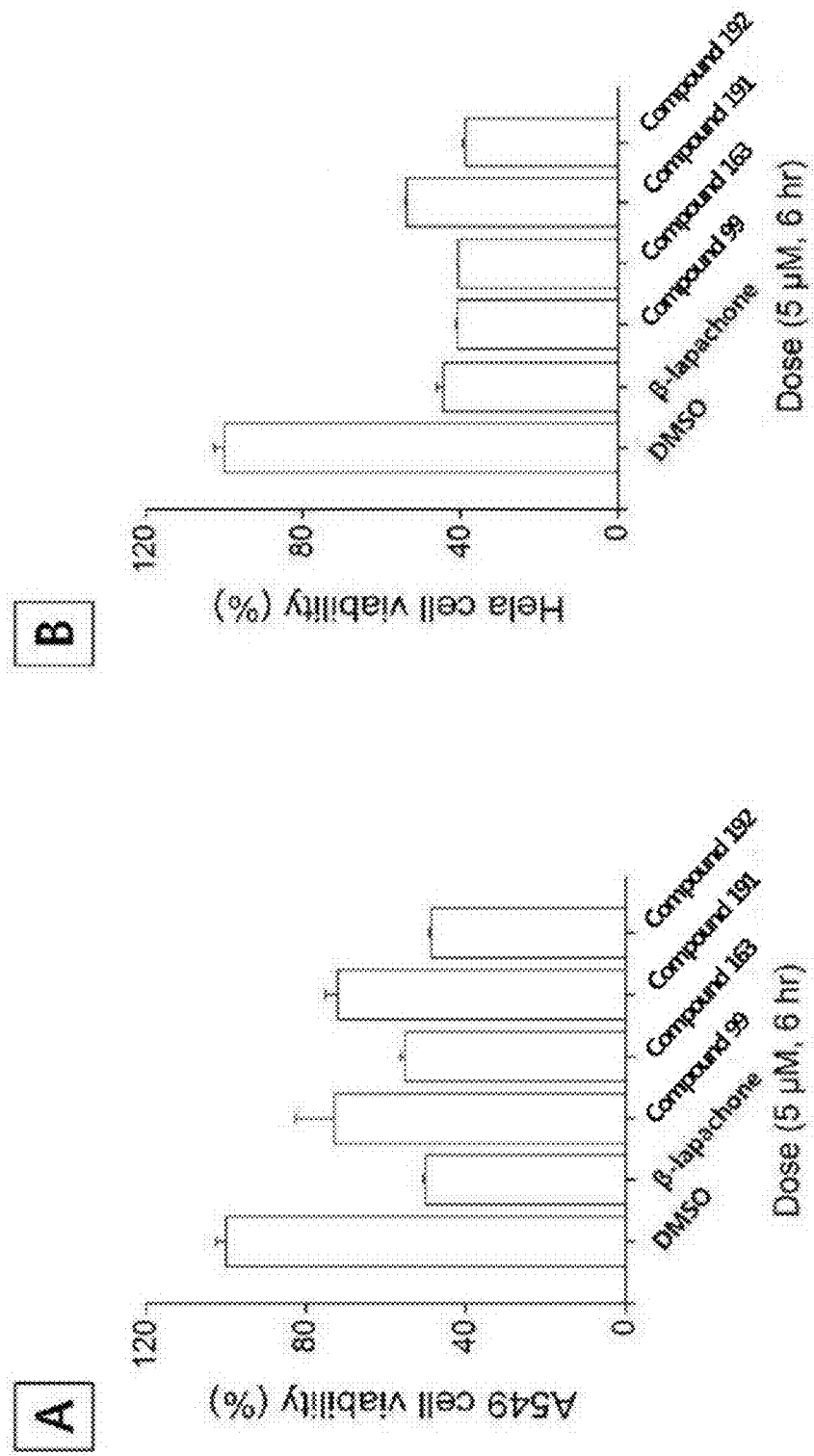
FIG. 5 depicts graphs showing cell survivability of A549 (lung carcinoma) and HeLa (cervix adenocarcinoma) cells when the A549 (lung carcinoma) and HeLa (cervix adenocarcinoma) cells were treated with compounds 99, 163, 191, and 192 of the present disclosure.

Referring to Table 6 and FIG. 5, compared with the controls, compounds 99, 163, 191, and 192 of the present disclosure, when were used to treat A549 (lung carcinoma), HeLa (cervix adenocarcinoma), HepG2 (hepatocellular carcinoma), MCF7 (breast adenocarcinoma), and Beas-2B (normal lung) cells, showed a similar cell-killing effect to β-lapachone, indicating that the compounds of the present disclosure had a treatment effect on solid cancer.

Although not shown in Table 6, the treatment of the normal lung cell line Beas-2B cells with the compounds of the present disclosure showed a cell viability of 80% or more on average, but the treatment of the lung carcinoma A549 cells showed a cell viability of about 50%. Therefore, the 1,2-naphthoquinone derivative compound of the present disclosure did not show cell toxicity on normal cells, but showed a cell-killing effect specifically on cancer cells, indicating that the 1,2-naphthoquinone derivative compound of the present disclosure can be helpfully used as a composition for treating various types of solid cancer.

Example 4-3: Measurement of Cell Viability of Solid Cancer Cells—CCK-8 Assay

To measure the cell viability of various types of solid cancer cells by CCK-8 assay, which is a method for quantifying cell counts through responses in mitochondria, the lung carcinoma cell line A549, the cervix adenocarcinoma cell line HeLa, the breast adenocarcinoma cell line MCF7, and the hepatocellular carcinoma cell line HepG2 were used.

The cells were incubated in 96-well plates at $2 \times 10^4$/well, and then were treated for 12 hours with the compounds of the present disclosure, which were dissolved in DMSO and diluted at a ratio of 1/2000 to a final concentration of 5 µM.

Thereafter, CCK-8 drug was added at 10 µl per well. After 30 minutes, the absorbance was measured using 450-nm and 595-nm filters by the microreader.

Figure 6:
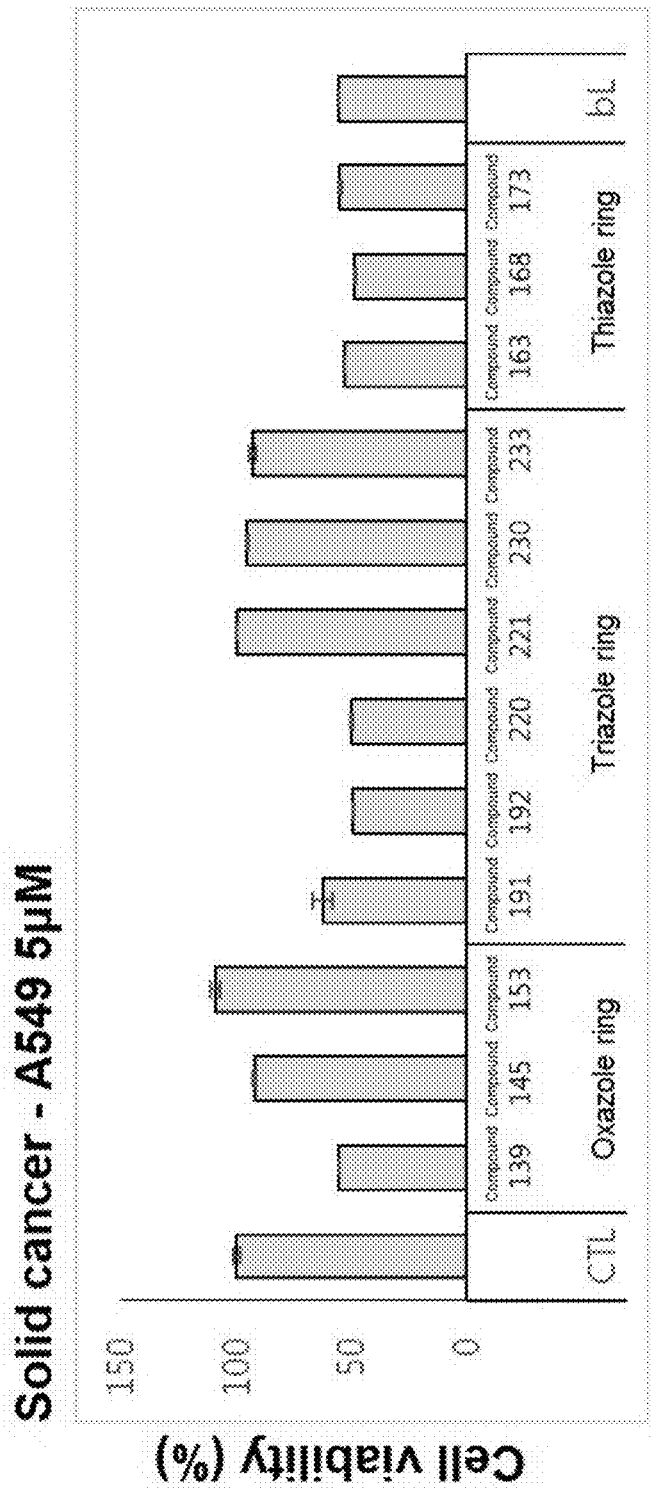
FIG. 6 is a graph showing cell viability of lung carcinoma A549 cells when the cells were treated with the compounds of the present disclosure.
Figure 7:
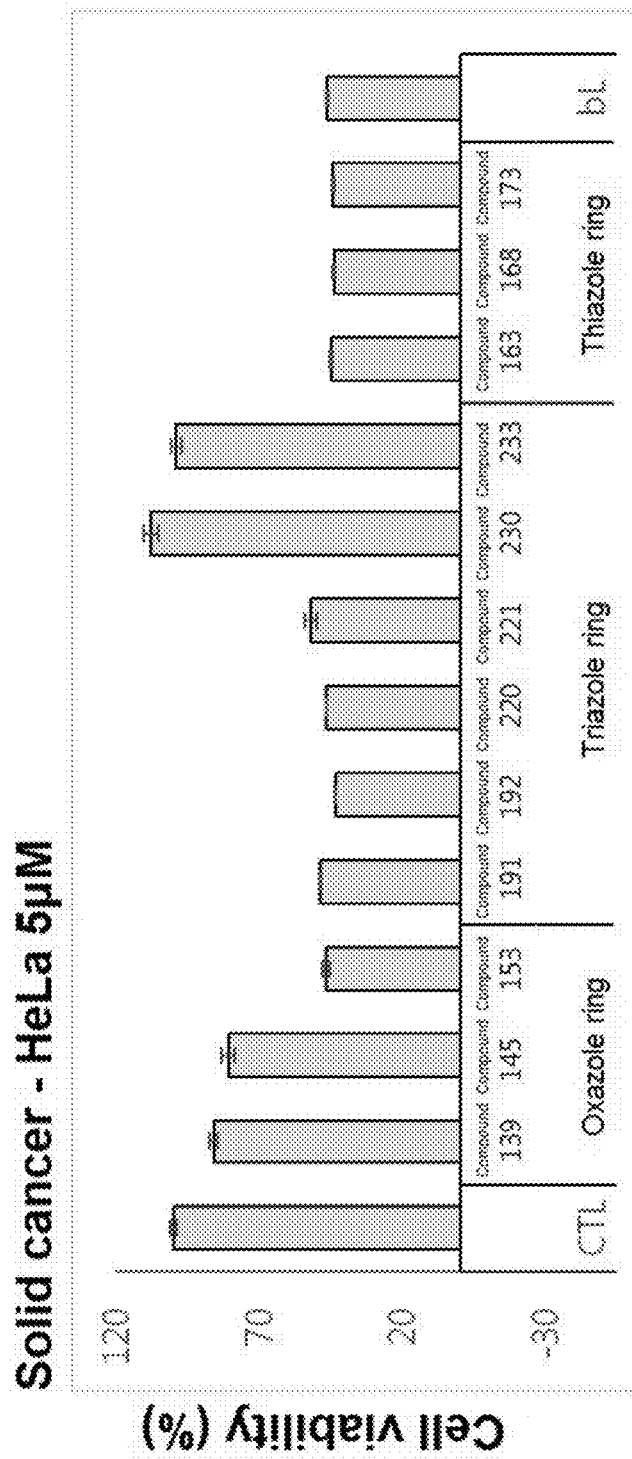
FIG. 7 is a graph showing cell viability of cervix adenocarcinoma HeLa cells when the cells were treated with the compounds of the present disclosure.
Figure 8:
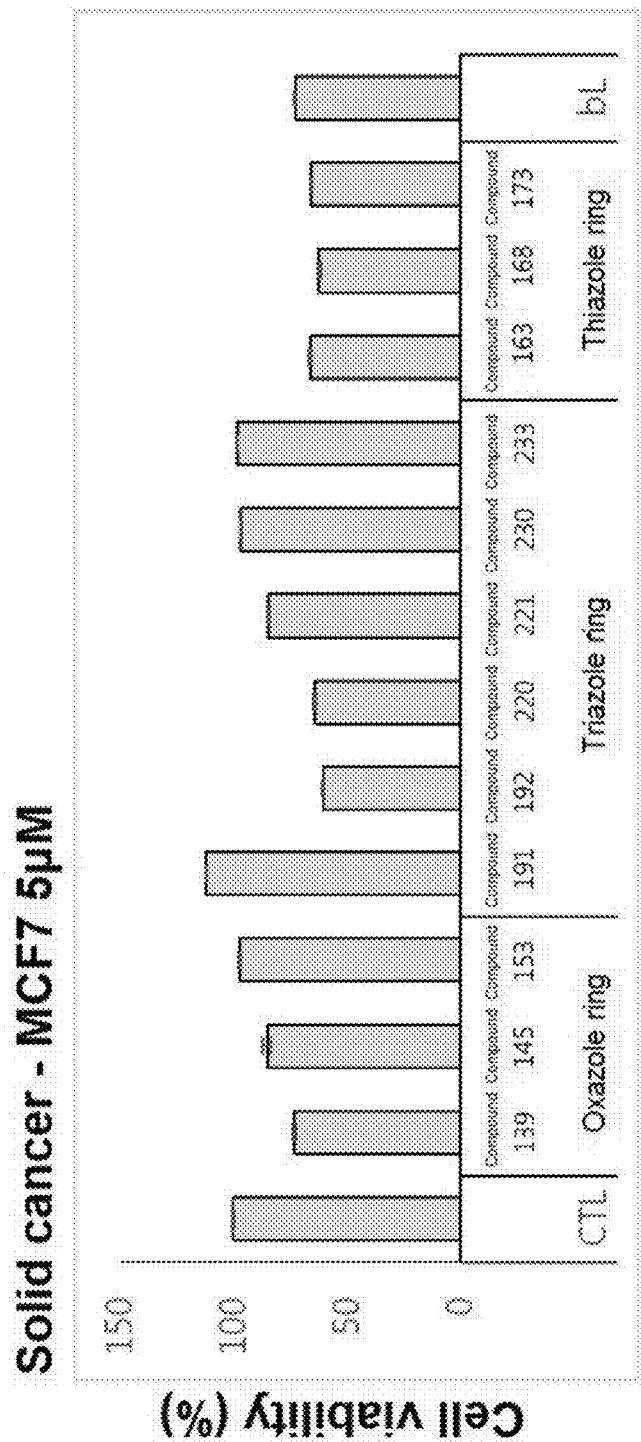
FIG. 8 is a graph showing cell viability of breast adenocarcinoma MCF7 cells when the cells were treated with the compounds of the present disclosure.
Figure 9:
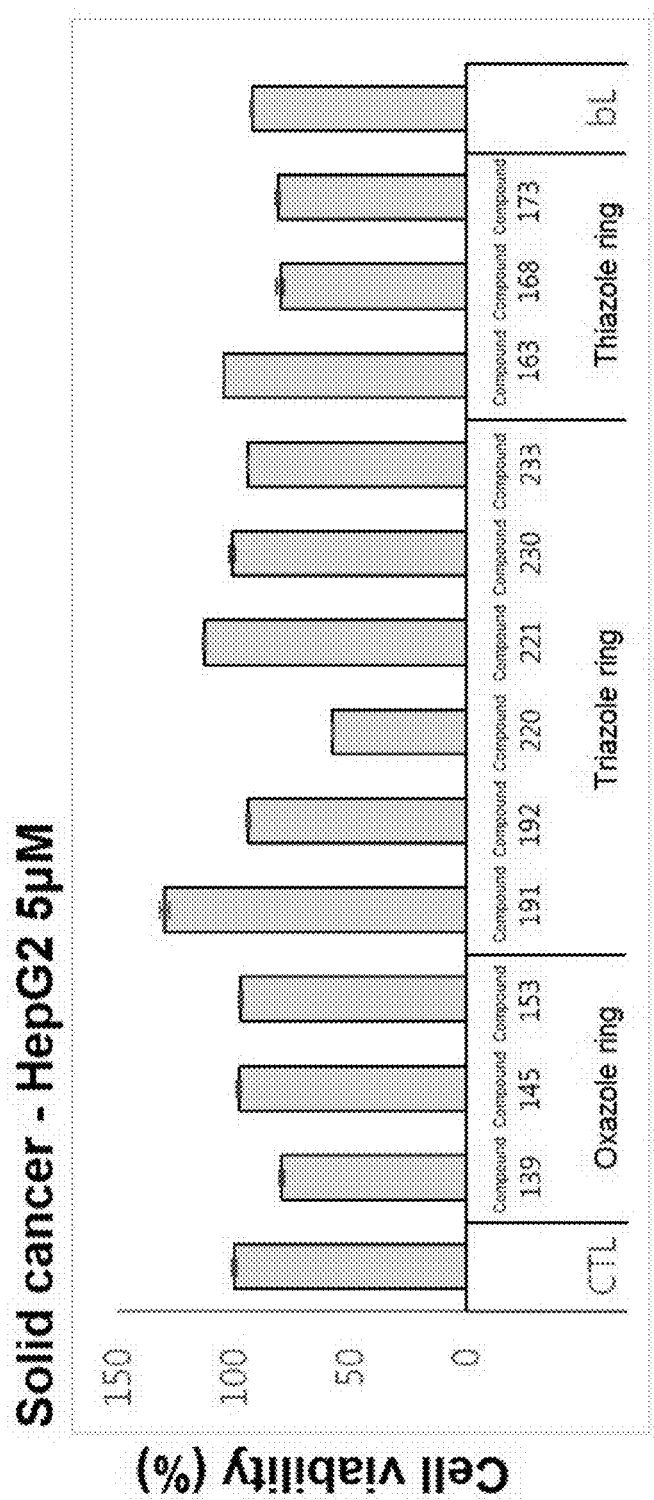
FIG. 9 is a graph showing cell viability of hepatocellular carcinoma HepG2 cells when the cells were treated with the compounds of the present disclosure.

A group treated with only DMSO is used as a control. On the basis of when the result of the control was considered to be 100%, the cell viability according to the treatment with the compounds of the present disclosure was identified, and the results are shown in FIGS. 6 and 9.

As shown in FIGS. 6 to 9, compared with previously known β-lapachone, the compounds of the present disclosure showed an excellent viability inhibitory effect on the lung carcinoma cell line A549, the cervix adenocarcinoma cell line HeLa, the breast adenocarcinoma cell line MCF7, and the hepatocellular carcinoma cell line HepG2, indicating that the compounds of the present disclosure showed an excellent anticancer effect on various types of solid cancer.

The invention claimed is:

1. A method for treating solid cancer or blood cancer, comprising administering to a patient in need thereof a therapeutically effective amount of a 1,2-naphotoquinone derivative compound represented by Formula 1 below or a pharmaceutically acceptable salt thereof:

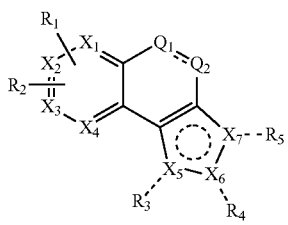

[Formula 1]

wherein, $R_1$ and $R_2$ are each independently hydrogen, halogen, hydroxy, $C_1$-$C_6$ alkoxy, $C_1$-$C_6$ alkyl, —$NO_2$, —$NR'_1R'_2$, —$NR'_1(CO(O)R'_2)$, —$NR'_1(C(O)NR'_1R'_2)$, —CN, wherein $R'_1$ and $R'_2$ are each independently hydrogen, or $C_1$-$C_6$ alkyl;

$R_3$ is hydrogen, halogen, hydroxy, $C_1$-$C_6$ alkyl, $C_1$-$C_6$ alkoxy, $C_3$-$C_8$ cycloalkyl, $(CR'_5R'_6)_m$—$C_4$-$C_{10}$ aryl, —$(CR'_5R'_6)_m$—$OR'_3$, or —$CO(O)R'_3$, wherein $R'_3$ is hydrogen, $C_1$-$C_6$ alkyl, $C_3$-$C_8$ cycloalkyl, $C_4$-$C_{10}$ aryl, —$(CR'_5R'_6)_m$—$C_4$-$C_{10}$ aryl, —$(CR'_5R'_6)_m$—$C_4$-$C_{10}$ aryloxy, —$(CR'_5R'_6)_m$—$C_1$-$C_{10}$ heteroaryl, or —CO(O)R''_3$, wherein $R'_5$ and $R'_6$ are each independently hydrogen or $C_1$-$C_3$ alkyl, and $R''_3$ is $C_1$-$C_6$ alkyl;

$R_4$ is hydrogen, halogen, hydroxy, $C_1$-$C_6$ alkyl, $C_2$-$C_{10}$ alkene, $C_1$-$C_6$ alkoxy, $C_3$-$C_8$ cycloalkyl, $C_2$-$C_8$ heterocycloalkyl, $C_4$-$C_{10}$ aryl, $C_4$-$C_{10}$ aryloxy, $C_1$-$C_8$ heteroaryl, —$(CR'_5R'_6)_m$—$C_4$-$C_{10}$ aryl, —$(CR'_5R'_6)_m$—$C_4$-$C_{10}$ aryloxy, —$(CR'_5R'_6)_m$—$C_1$-$C_8$ heteroaryl, —$(CR'_5R'_6)_m$—$NR'_3R'_4$, —$(CR'_5R'_6)_m$—$C_3$-$C_8$ heterocycloalkyl, —$(CR'_5R'_6)_m$—$OR'_3$, —$(CR'_5R'_6)_m(O)COR'_3$, —$CO(O)R'_3$, —$CONR'_3R'_4$, —$NR'_3R'_4$, or —$NR'_3(C(O)R'_4)$, wherein $R'_3$ and $R'_4$ are each independently hydrogen, $C_1$-$C_6$ alkyl, $C_3$-$C_8$ cycloalkyl, $C_4$-$C_{10}$ aryl, —$(CR'_5R'_6)_m$—$C_4$-$C_{10}$ aryl, —$(CR'_5R'_6)_m$—$C_4$-$C_{10}$ aryloxy, —$(CR'_5R'_6)_m$—$C_1$-$C_{10}$ heteroaryl, or —CO(O)R''_3$, or $R'_3$ and $R'_4$ may form a cyclic structure of $C_2$-$C_{10}$ heterocycloalkyl or a cyclic structure of $C_1$-$C_{10}$ heteroaryl by mutual coupling, and $R'_5$ and $R'_6$ are each independently hydrogen or $C_1$-$C_3$ alkyl, wherein $R''_3$ is $C_1$-$C_6$ alkyl;

$R_5$ is hydrogen, halogen, hydroxy, $C_1$-$C_6$ alkyl, $C_2$-$C_{10}$ alkene, $C_1$-$C_6$ alkoxy, $C_3$-$C_8$ cycloalkyl, $C_2$-$C_8$ heterocycloalkyl, $C_4$-$C_{10}$ aryl, $C_4$-$C_{10}$ aryloxy, $C_1$-$C_8$ heteroaryl, —$(CR'_5R'_6)_m$—$C_4$-$C_{10}$ aryl, —$(CR'_5R'_6)_m$—$C_4$-$C_{10}$ aryloxy, —$(CR'_5R'_6)_m$—$C_1$-$C_8$ heteroaryl, —$(CR'_5R'_6)_m$—$NR'_3R'_4$, —$(CR'_5R'_6)_m$—$C_3$-$C_8$ heterocycloalkyl, —$(CR'_5R'_6)_m$—$OR'_3$, —$(CR'_5R'_6)_m(O)COR'_3$, —$CO(O)R'_3$, —$CONR'_3R'_4$, —$NR'_3R'_4$, or —$NR'_3(C(O)R'_4)$, wherein $R'_3$ and $R'_4$ are each independently hydrogen, $C_1$-$C_6$ alkyl, $C_3$-$C_8$ cycloalkyl, $C_4$-$C_{10}$ aryl, —$(CR'_5R'_6)_m$—$C_4$-$C_{10}$ aryl, —$(CR'_5R'_6)_m$—$C_4$-$C_{10}$ aryloxy, —$(CR'_5R'_6)_m$—$C_1$-$C_{10}$ heteroaryl, or —CO(O)R''_3$, or $R'_3$ and $R'_4$ may form a cyclic structure of $C_2$-$C_{10}$ heterocycloalkyl or a cyclic structure of $C_1$-$C_{10}$ heteroaryl by mutual coupling, and R's and $R'_6$ are each independently hydrogen or $C_1$-$C_3$ alkyl, wherein $R''_3$ is $C_1$-$C_6$ alkyl, $Q_1$ and $Q_2$ are each CO;

m and m' are each independently an integer of 1 to 4;

a heteroatom is at least one selected from N, O, and S;

$X_1$ to $X_4$ are each independently CH or N(R''_6), wherein R''_6 is hydrogen or $C_1$-$C_3$ alkyl;

$X_5$, $X_6$, and $X_7$ are N; and the sign ---- represents a single bond or represents that a bond may not be formed, and the sign

in the Formula 1 represents that a cyclic structure containing the sign may be or may not be an aromatic structure.

2. A method for treating solid cancer or blood cancer, comprising administering to a patient in need thereof a therapeutically effective amount of at least one of the following 1,2-naphtoquinone derivative compounds or pharmaceutically acceptable salts thereof:

Compound 105

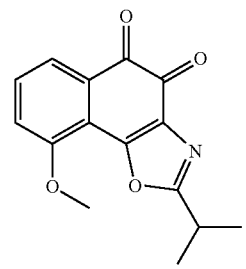

-continued
Compound 106
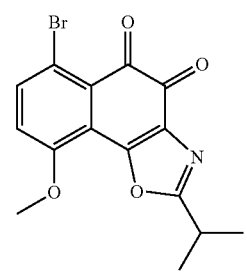
Compound 107
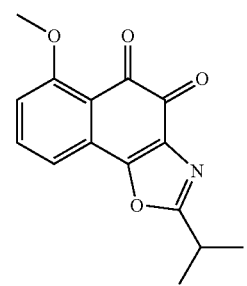
Compound 108
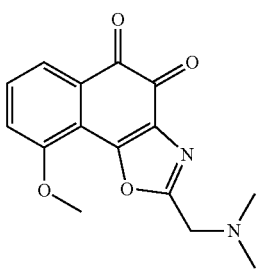
Compound 109
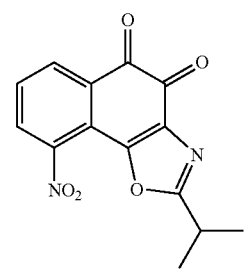
Compound 110
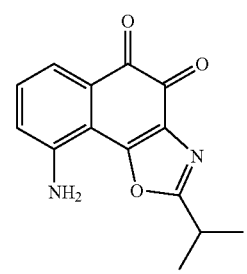
Compound 111
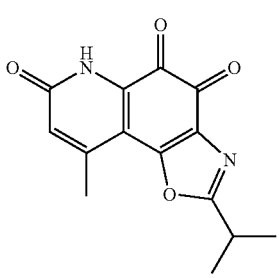
-continued
Compound 112
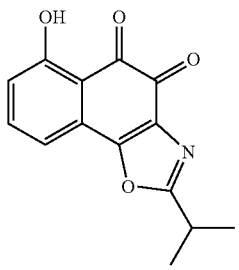
Compound 113
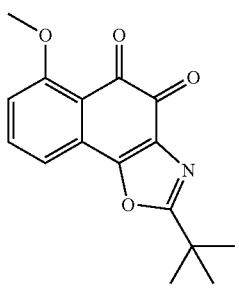
Compound 114
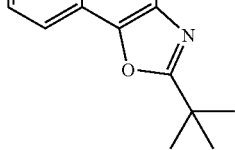
Compound 115
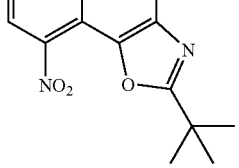
Compound 116
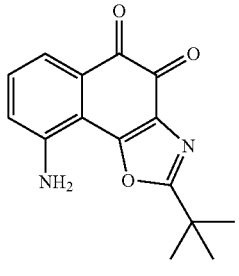
Compound 117
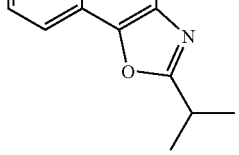

Compound 118
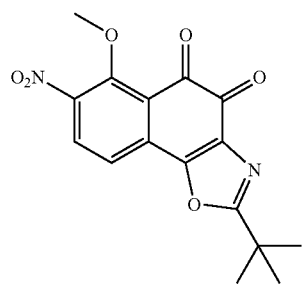
Compound 119
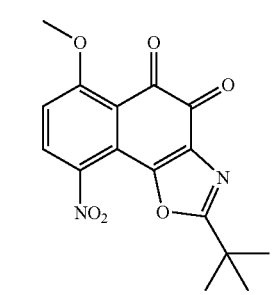
Compound 120
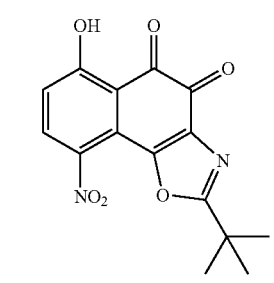
Compound 121
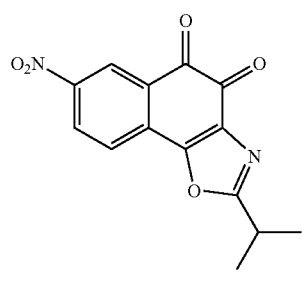
Compound 122
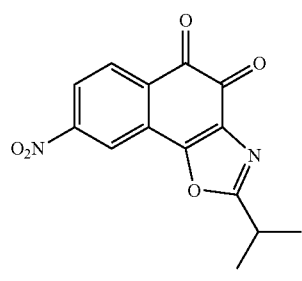
Compound 123
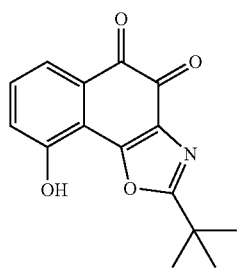
Compound 124
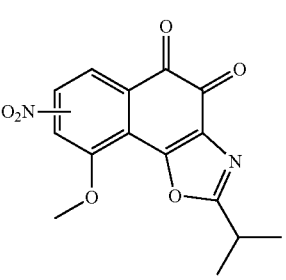
Compound 125
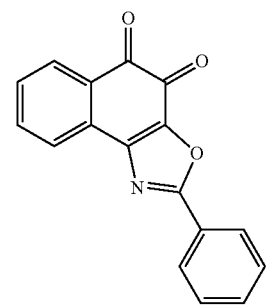
Compound 126
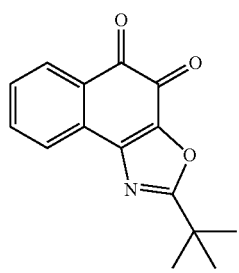
Compound 127
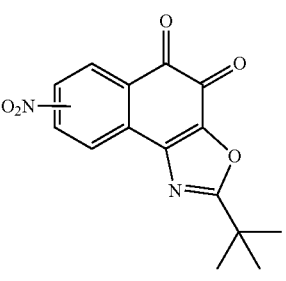

-continued
Compound 128
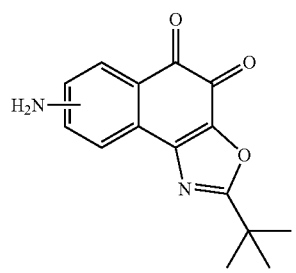
Compound 129
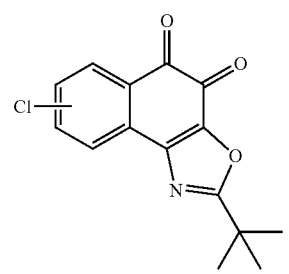
Compound 130
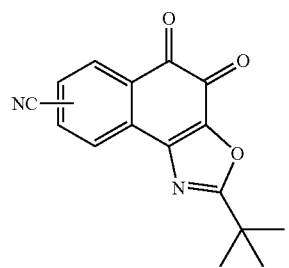
Compound 131
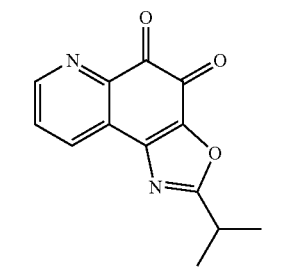
Compound 132
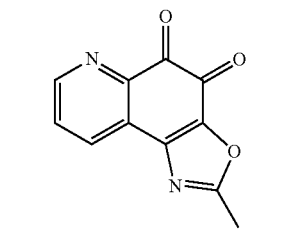
Compound 133
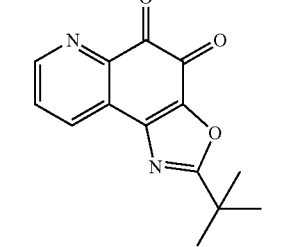
-continued
Compound 134
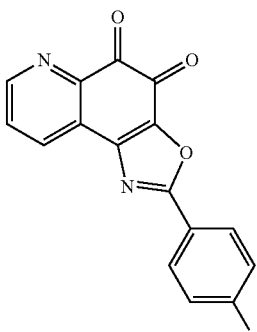
Compound 135
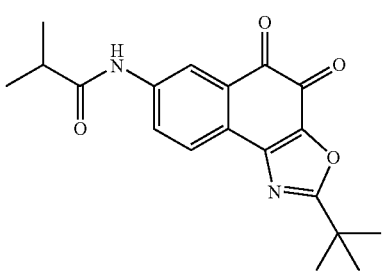
Compound 136
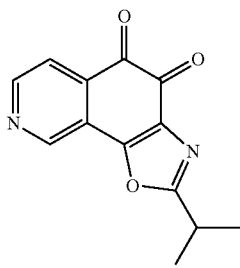
Compound 137
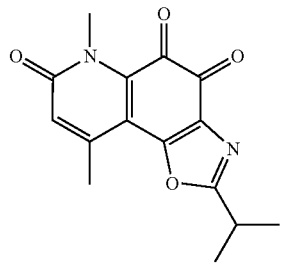
Compound 138
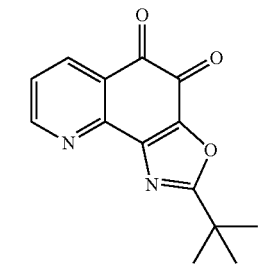

Compound 139
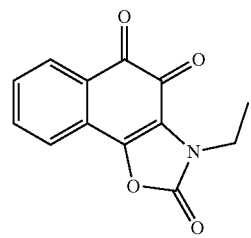
Compound 140
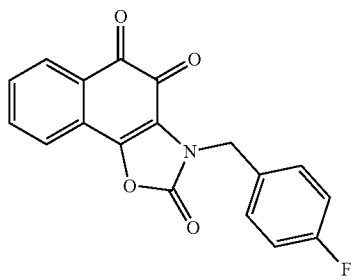
Compound 141
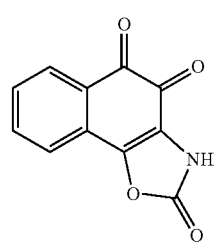
Compound 150
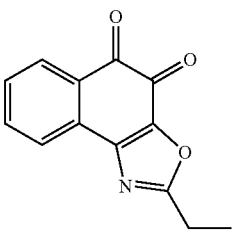
Compound 151
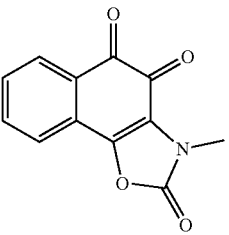
Compound 156
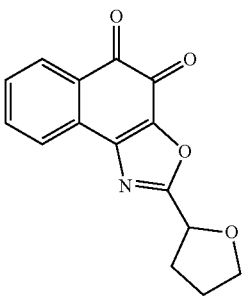
Compound 162
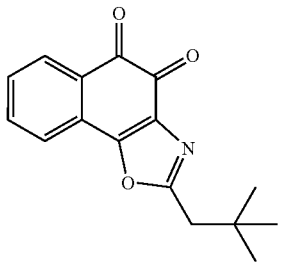
Compound 163
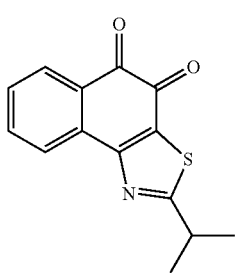
Compound 164
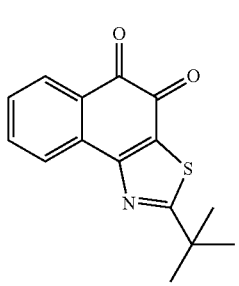
Compound 165
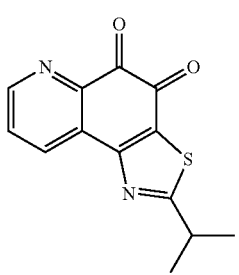
Compound 166
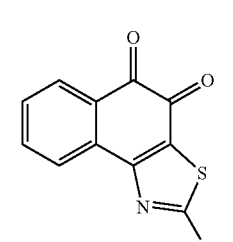
Compound 167
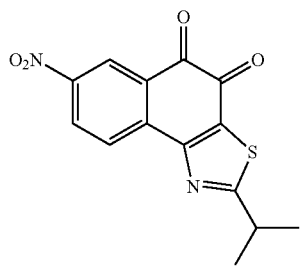

51
-continued

Compound 168

Compound 169

Compound 170

Compound 171

Compound 172

52
-continued

Compound 173

Compound 174

Compound 191

Compound 192

Compound 193

Compound 194

Compound 195
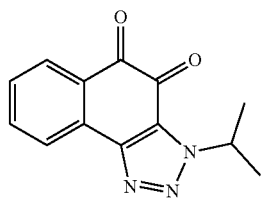
Compound 196
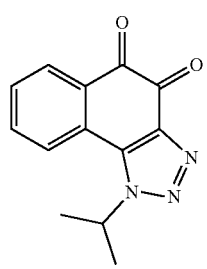
Compound 197
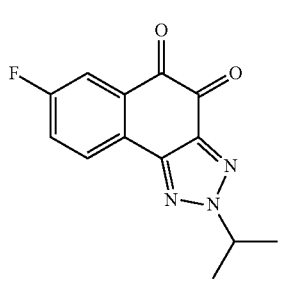
Compound 198
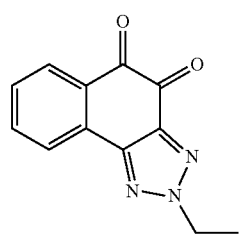
Compound 199
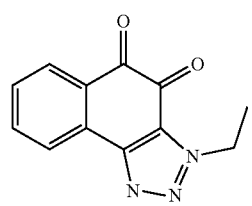
Compound 200
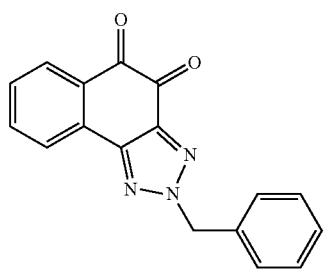
Compound 201
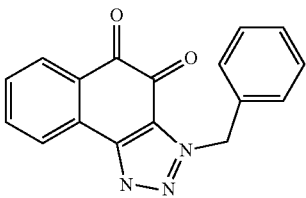
Compound 202
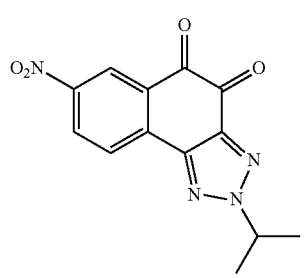
Compound 203
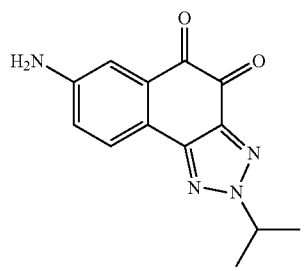
Compound 204
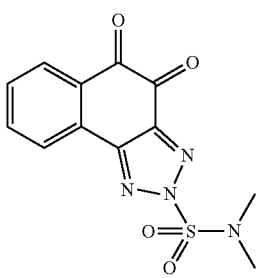
Compound 205
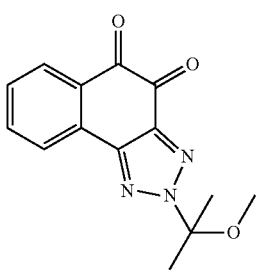
Compound 206
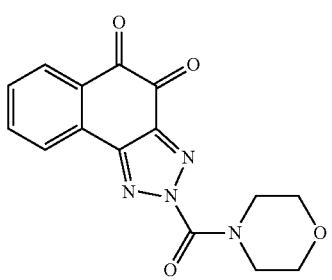

Compound 207
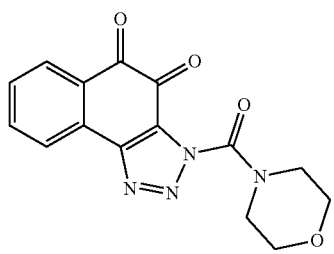
Compound 208
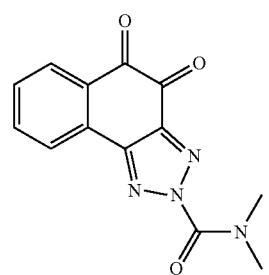
Compound 209
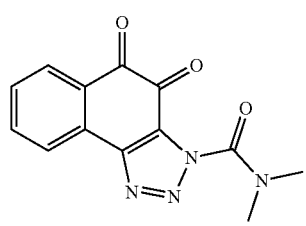
Compound 210
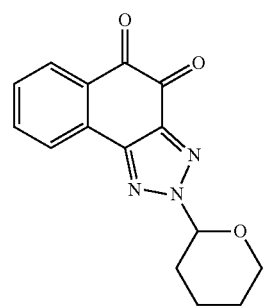
Compound 211
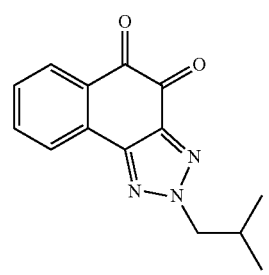
Compound 212
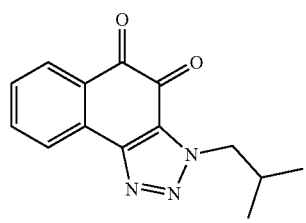
Compound 213
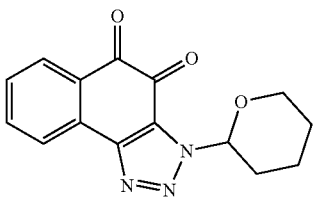
Compound 214
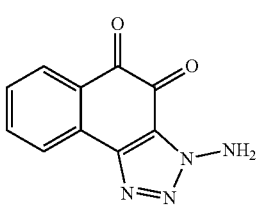
Compound 215
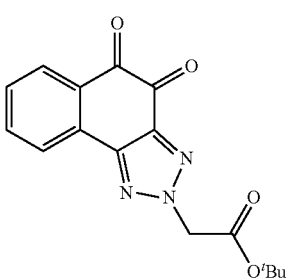
Compound 216
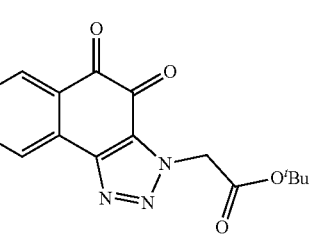
Compound 217
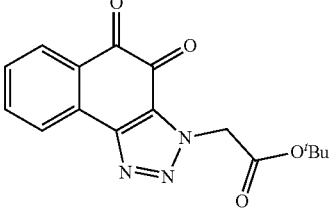
Compound 218
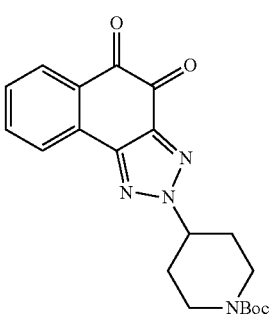

Compound 219
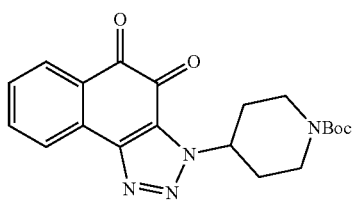
Compound 220
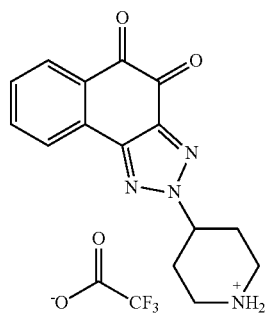
Compound 221
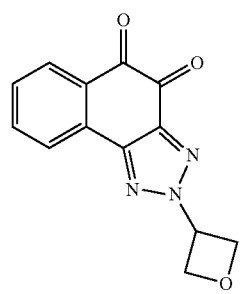
Compoound 222
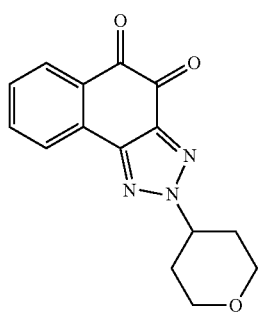
Compound 223
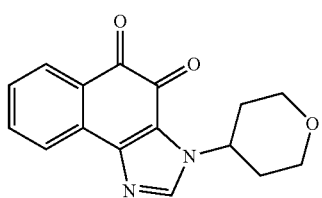
Compound 224
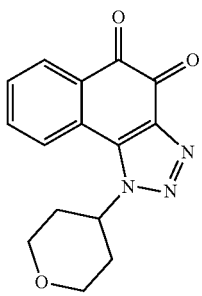
Compound 225
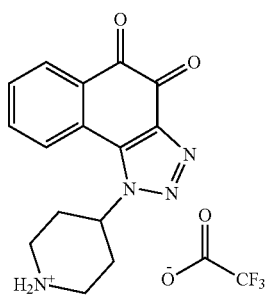
Compound 226
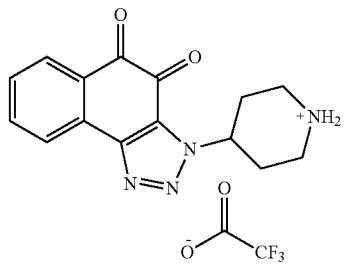
Compound 227
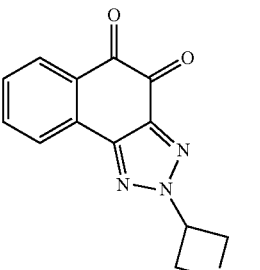
Compound 228
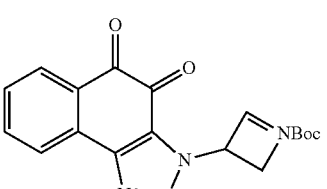
Compound 229
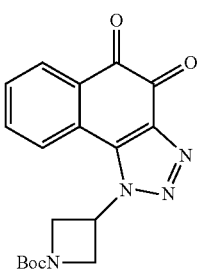

-continued
Compound 230
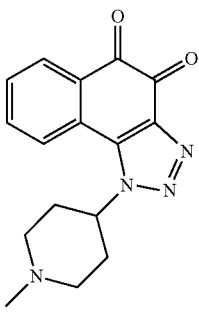
Compound 231
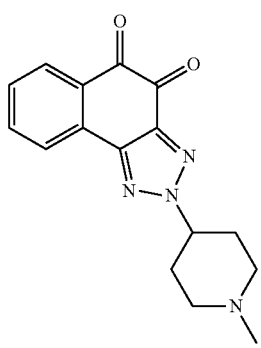
Compound 232
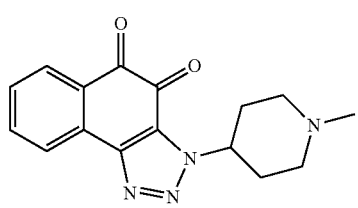
Compound 233
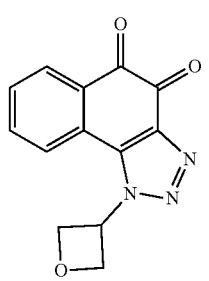
or
Compound 234
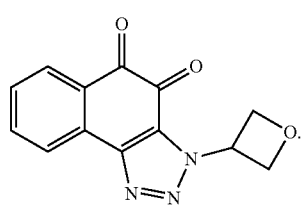
3. The method of claim 2, wherein the compound is at least one of the following compounds:
Compound 151
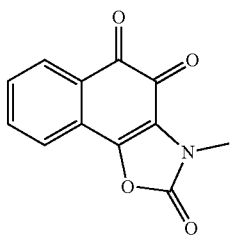
Compound 156
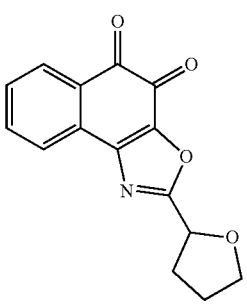
Compound 172
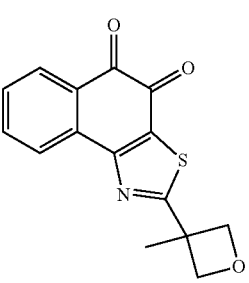
Compound 173
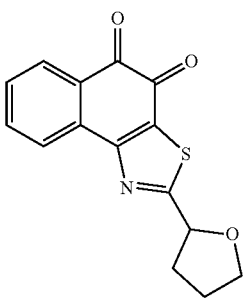
Compound 174
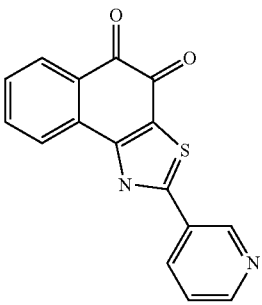

-continued

Compoound 230

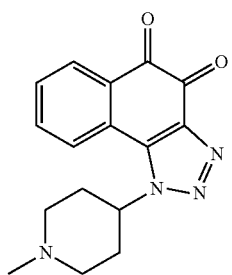

Compound 231

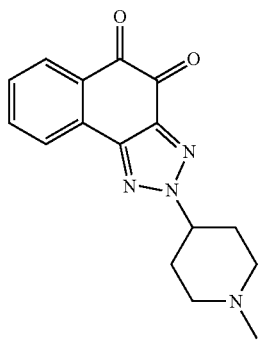

Compound 232

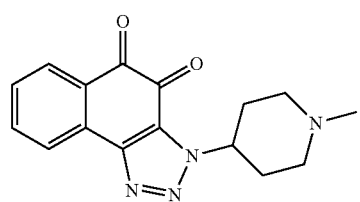

Compound 233

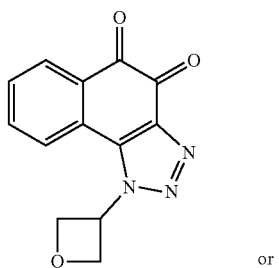

or

-continued

Compound 234

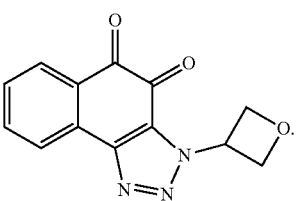

4. The method of claim 1, wherein the blood cancer is selected from the group consisting of acute leukemia, chronic leukemia, drug-resistant chronic leukemia, and refractory acute leukemia.

5. The method of claim 4, wherein the chronic leukemia is chronic myeloid leukemia or chronic lymphocytic leukemia.

6. The method of claim 4, wherein the acute leukemia is acute myeloid leukemia or acute lymphoblastic leukemia.

7. The method of claim 1, wherein the solid cancer is selected from the group consisting of lung cancer, uterine cancer, liver cancer, and breast cancer.

8. The method of claim 2, wherein the blood cancer is selected from the group consisting of acute leukemia, chronic leukemia, drug-resistant chronic leukemia, and refractory acute leukemia.

9. The method of claim 2, wherein the solid cancer is selected from the group consisting of lung cancer, uterine cancer, liver cancer, and breast cancer.

10. The method of claim 8, wherein the chronic leukemia is chronic myeloid leukemia or chronic lymphocytic leukemia.

11. The method of claim 8, wherein the acute leukemia is acute myeloid leukemia or acute lymphoblastic leukemia.

* * * * *